(12) United States Patent
Caspi et al.

(10) Patent No.: US 10,512,671 B2
(45) Date of Patent: Dec. 24, 2019

(54) IL-24 TO TREAT INFLAMMATORY DISEASES

(71) Applicant: THE UNITED STATES OF AMERICA, as represented by the Secretary, Department of Health and Human Services, Bethesda, MD (US)

(72) Inventors: Rachel R. Caspi, Bethesda, MD (US); Wai Po Chong, Mongkok (HK); Reiko Yamane, Rockville, MD (US); Mary Mattapallil, Rockville, MD (US)

(73) Assignee: THE UNITED STATES OF AMERICA, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 15/957,019

(22) Filed: Apr. 19, 2018

(65) Prior Publication Data

US 2018/0303906 A1  Oct. 25, 2018

Related U.S. Application Data

(60) Provisional application No. 62/487,223, filed on Apr. 19, 2017.

(51) Int. Cl.
| | | |
|---|---|---|
| *A61K 38/20* | (2006.01) | |
| *A61K 47/68* | (2017.01) | |
| *A61K 38/17* | (2006.01) | |
| *A61K 38/22* | (2006.01) | |
| *A61P 27/02* | (2006.01) | |
| *A61K 9/00* | (2006.01) | |
| *A61P 37/06* | (2006.01) | |

(52) U.S. Cl.
CPC ............ *A61K 38/20* (2013.01); *A61K 9/0019* (2013.01); *A61K 38/1774* (2013.01); *A61K 38/22* (2013.01); *A61K 47/68* (2017.08); *A61P 27/02* (2018.01); *A61P 37/06* (2018.01); *A61K 9/0048* (2013.01)

(58) Field of Classification Search
None
See application file for complete search history.

(56) References Cited

PUBLICATIONS

Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*
Chong et al, "IL-17A is dispensable for autoimmune tissue damage in the neuroretina and negatively regulates the Th17 cytokine program," Poster presented at 4th Meeting of the International Cytokine and Interferon Society (ICIS), Oct. 2016.

* cited by examiner

*Primary Examiner* — Bridget E Bunner
*Assistant Examiner* — Fozia M Hamud
(74) *Attorney, Agent, or Firm* — Klarquist Sparkman, LLP

(57) ABSTRACT

Methods are provided for treating ocular surface inflammation and/or uveitis in a subject. The methods can include selecting a subject with uveitis and/or ocular surface disease. The methods can then include administering to the subject a therapeutically effective amount of an interleukin 24 (IL-24) polypeptide or nucleic acid encoding the IL-24 polypeptide. In some examples, the administered IL-24 polypeptide suppresses production of effector cytokines by Th17 cells. A pharmaceutical composition is further provided here that includes an IL-24 polypeptide or nucleic acid encoding the polypeptide. In some examples, the IL-24 polypeptide is a variant of IL-24 or an Fc fusion protein that includes IL-24. The pharmaceutical composition can be used in any of the methods provided herein to treat ocular surface inflammation and/or uveitis.

24 Claims, 12 Drawing Sheets

Specification includes a Sequence Listing.

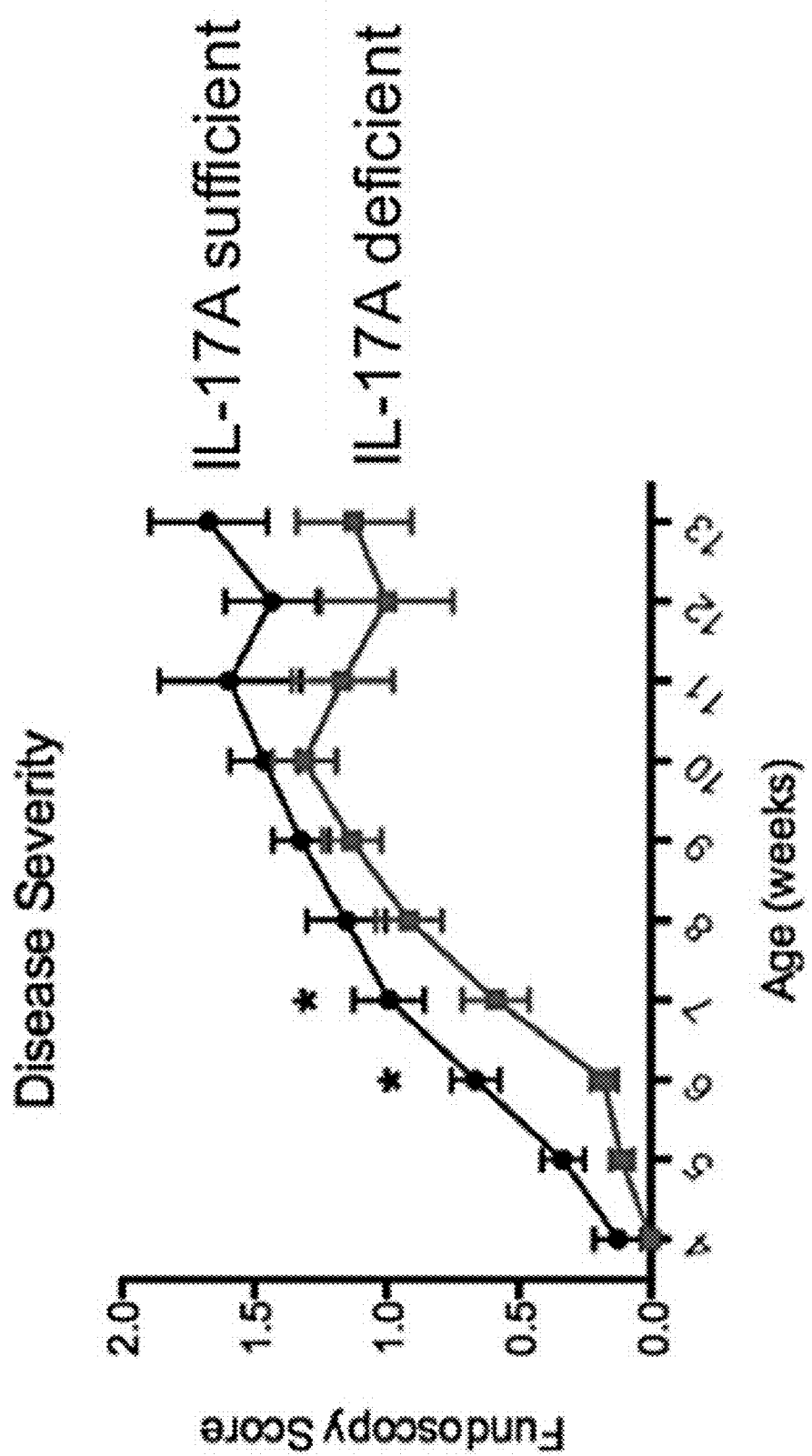

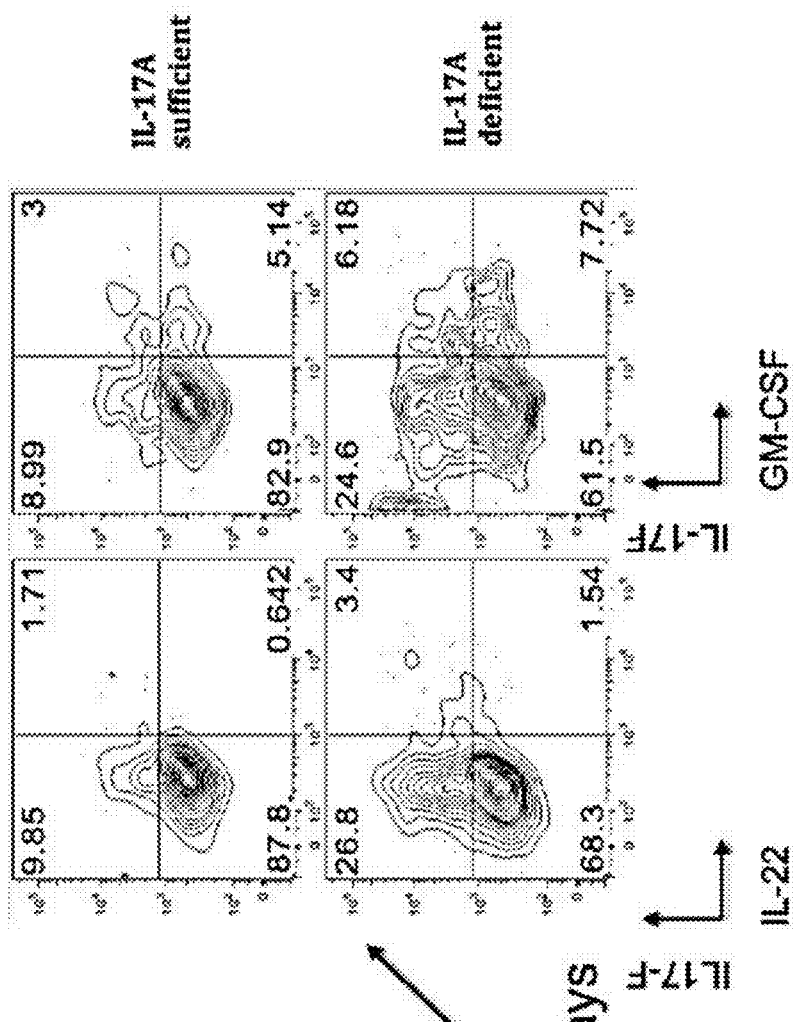
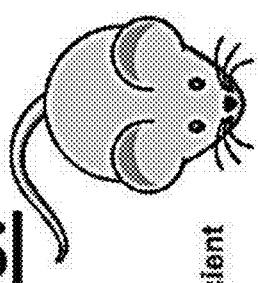
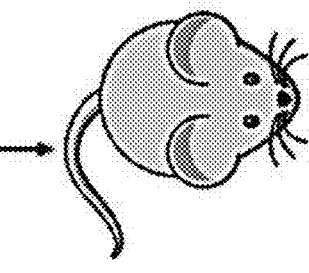
FIG. 4A
FIG. 4B

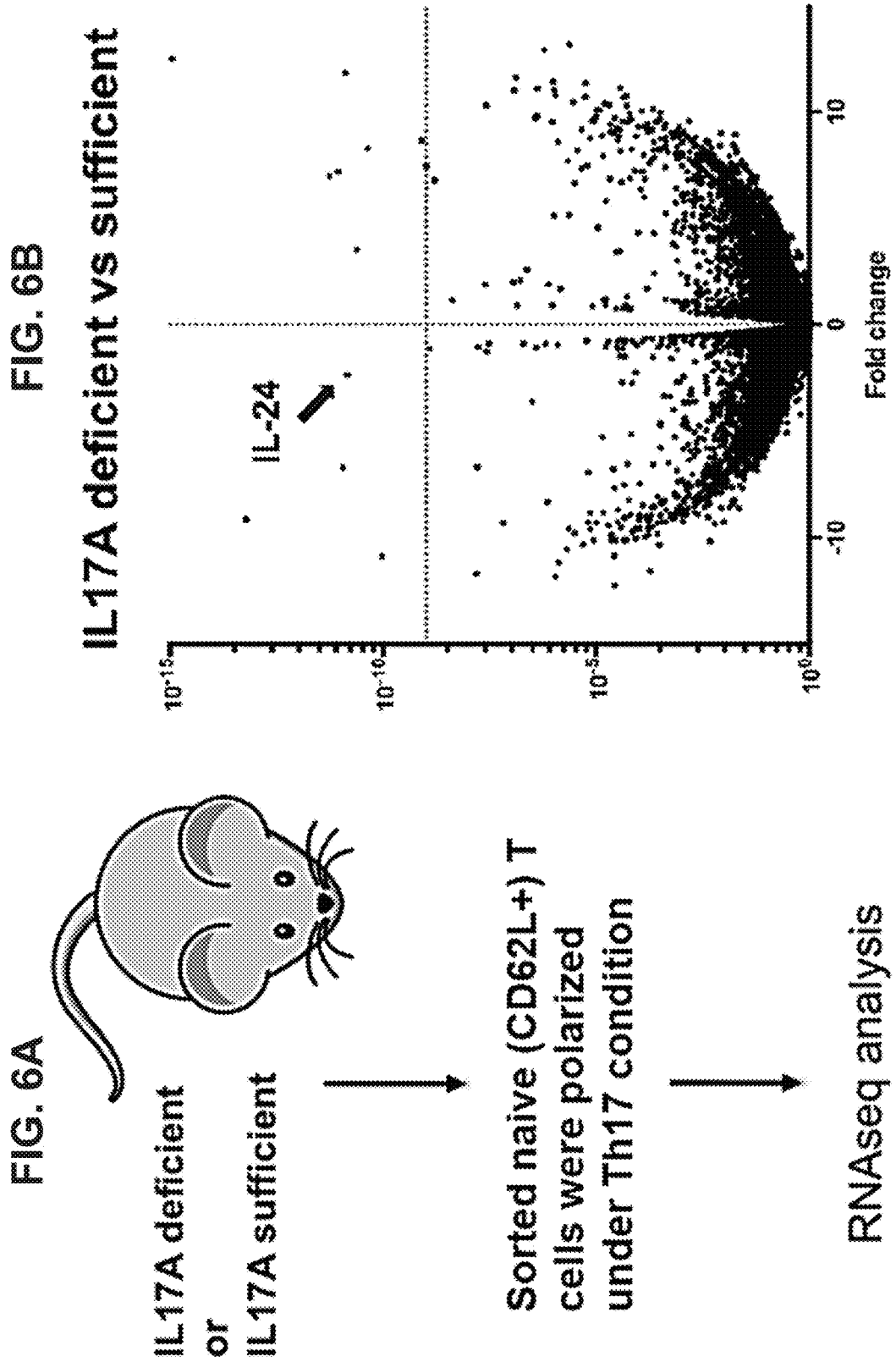

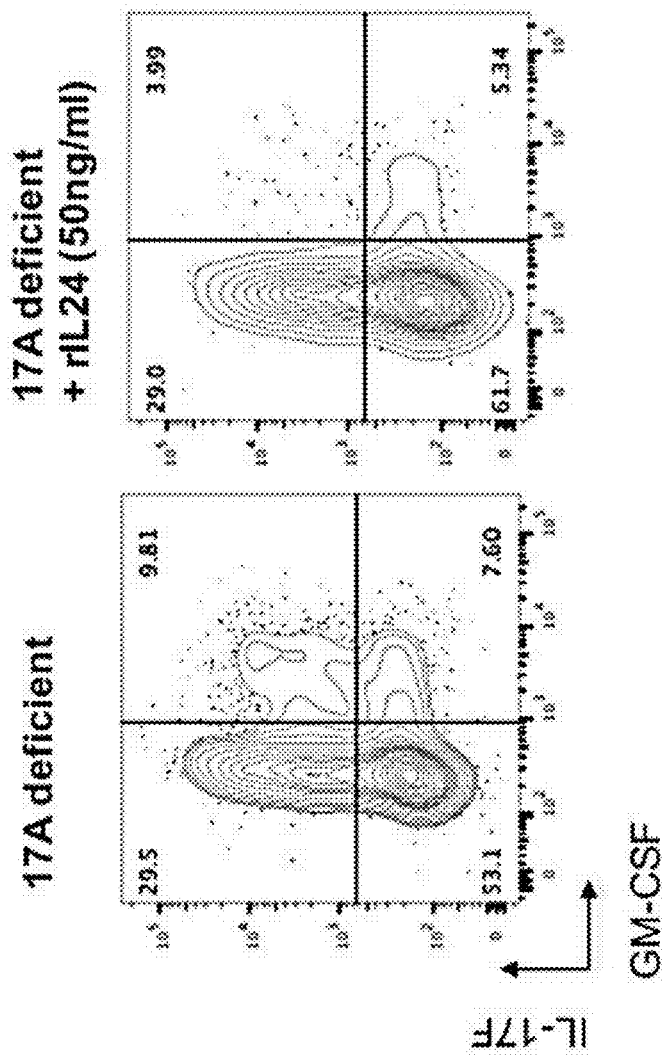
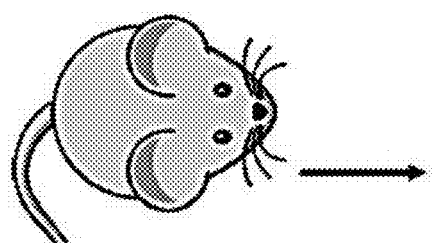

FIG. 12

```
NP_001172085    1    M-------NFQQRLQBLWTLASRPFCPP--LLATASQWQMVLPCLGFTLLLWSQVSAQGQEFHFGPCQVKGVVP    67
NP_444325       1    MLTEDAQLFVRRKWQPSEHSSLRLHFRTLAGALALSSTQMSWGLQILPCLSLILLLWNQVPCLBGQEFRFGSLQVTGVVL    80

NP_001172085    68   QKLWEAFWAVKDTMQAQDMTFSARLLQQEVLAQNVSDAESCYLVBFLLEFYLKTVFKMYHNKFVEVRCLLKSFSILANEFYL   147
NP_444325       81   PEIWEAFWTVKNFVQTQDDITTSIRLLIKPQVLRNVSGAESCYLAHSLLKFYLNTVFKMYHSKIAKPKVLRSFSTLANEFIV   160

NP_001172085    148  IVSQLQPSQENEMFSIRQSAHRRPLLFRRAFKQLDVEAALTKALGEVDILLLWMQKFYXL   207
NP_444325       161  IHSQLQPSKDNSMLPISESAHQRPLLFRRAFKQLDTEVALVKAFGEVDILLTWMQKFYHL   220
```

IL-24 TO TREAT INFLAMMATORY DISEASES

CROSS REFERENCE TO RELATED APPLICATIONS

This application claims the benefit of U.S. Provisional Application No. 62/487,223, filed Apr. 19, 2017, which is herein incorporated by reference in its entirety.

ACKNOWLEDGMENT OF GOVERNMENT SUPPORT

This invention was made with Government support under project number Z01EY000184 awarded by the National Institutes of Health, National Eye Institute. The Government has certain rights in the invention.

FIELD

This disclosure relates to methods and compositions for treating ocular inflammatory disease, such as using IL-24.

BACKGROUND

T helper type 17 (Th17) lymphocytes are characterized by the production of interleukin (IL)-17; these cells are involved in many autoimmune disorders. Th17 cells are also involved in ocular inflammatory diseases, such as uveitis, scleritis, dry eye syndrome, and corneal inflammation (see Kang et al., *J. Korean Med. Sci.* 26: 938-944, 2011).

Intraocular inflammatory diseases grouped under the term "uveitis" are a major cause of visual loss in industrialized nations. "Uveitis" refers to an intraocular inflammation of the uveal tract, namely, the iris, choroids, and ciliary body. Uveitis is responsible for about 10% of legal blindness in the United States (National Institutes of Health, *Interim Report of the Advisory Eye Council Support for Visual Research*, U.S. Department of Health Education and Welfare, Washington, D.C., 1976, pp. 20-22). Complications associated with uveitis include posterior synechia, cataract, glaucoma, and retinal edema (Smith et al., *Immunol. Cell Biol.* 76:497-512, 1998).

Autoimmune uveitis is a sight-threatening disease driven by retina-specific T cells that target the neuroretina of the eye; studies in animal models of experimental autoimmune uveitis (EAU) indicate that Th17 cells are a major effector population. The Th17 response and IL-17A have been associated with host defense as well as with autoimmune diseases in patients and in experimental animal models. IL-17A is recognized as the Th17 signature cytokine, and IL-17A-producing T cells are pathogenic effectors in models of autoimmunity, including experimental autoimmune uveitis (EAU) induced by immunization with the retinal protein IRBP in complete Freund's adjuvant.

Treatment of uveitis often focuses on control of the inflammatory symptoms. In such cases, corticosteroids are often used to suppress inflammation in the eye. Anterior uveitis often responds to local steroid treatment with eye drops. However, drops do not usually provide therapeutic levels of steroids in the posterior part of the eye for the treatment of posterior uveitis or panuveitis. Periocular injections are then indicated. These injections can be given sub-conjunctively or beneath Tenon's capsule.

Systemic treatments with corticosteroids are often used when local injections fail. However, many of the most severe cases of uveitis do not respond to high-dose systemic corticosteroid therapy. In addition, the side effects of such systemic therapies can include hypertension, hyperglycemia, peptic ulceration, Cushingoid features, osteoporosis, growth limitation, myopathy, psychosis, and increased susceptibility to infection, which can be devastating. Finally, many of the local and systemic steroid therapies also have potentially sight-threatening side effects, such as glaucoma, cataract, and susceptibility to eye infection. Newer immunosuppressive agents are being investigated for use in uveitis treatment, such as tacrolimus, sirolimus, and mycophelonate mofetil. However, these drugs also have serious side effects (Anglade and Whitcup, *Drugs* 49:213-223, 1995). Therefore, there exists a need for new methods to treat inflammatory disease of the eye.

SUMMARY

It is disclosed herein that injection of IL-17 ameliorates experimental autoimmune uveitis (EAU). This is unexpected, as the Th17 response and IL-17A are associated with autoimmune diseases and IL-17A-producing T cells are pathogenic effectors in models of autoimmunity, such as EAU. In addition, gene expression profiling showed lower IL-24 expression in Th17 cells in association with IL-17A deficiency, and IL-24 suppressed production of effector cytokines by Th17 cells and inhibited their ability to induce EAU.

In some embodiments, methods are disclosed herein for treating ocular surface inflammation or uveitis. These methods include administration of a therapeutically effective amount of IL-24 polypeptides and/or polynucleotides encoding IL-24 polypeptides. The subject can be a mammalian subject, such as a human subject. In some examples, the methods include selecting a subject with uveitis. In further examples, the methods include selecting a subject with an ocular surface disease. The subject can be a mammalian subject, such as a human.

In additional embodiments, a pharmaceutical composition is disclosed herein that includes an IL-24 polypeptide, a variant thereof, or an Fc fusion protein thereof. In some examples, the polypeptide, variant, or Fc fusion protein suppresses production of effector cytokines by Th17 cells. In some examples, the pharmaceutical composition includes a nucleic acid that encodes the IL-24 polypeptide, variant thereof, or Fc fusion protein thereof. In some examples, the pharmaceutical composition is used in any of the disclosed methods to treat ocular surface inflammation or uveitis.

The foregoing and other objects, features, and advantages of the invention will become more apparent from the following detailed description, which proceeds with reference to the accompanying figures.

BRIEF DESCRIPTION OF THE DRAWINGS

FIG. 1 shows that systemic interleukin (IL)-17A deficiency in R161H mice does not affect disease severity. The disease severity of IL-17A-sufficient mice (circles) was compared with the disease severity of IL-17A-deficient mice (squares).

FIGS. 4A-4B show that IL-17A-deficient Th17 cells (bottom) produce higher levels of Th17-related cytokines (IL-17F and IL-22 (left) as well as GM-CSF (right)) in vivo compared with IL-17A-sufficient Th17 cells (top).

FIGS. 6A-6B show that IL-17 deficiency enhances expression of the IL-24 gene using gene expression profiling of IL-17A-sufficient and IL-17A-deficient Th17 cells.

FIGS. 7A-7B compare IL-17A-deficient Th17 cell (left) production of Th17-related cytokines (IL-17F and GM-CSF) in vitro compared with IL-17A-sufficient Th17 cells (left); rIL-24 was then added (right).

FIG. 12 is a sequence comparison that documents that there is 70% identity between IL-24 proteins of human and mouse by BLAST (BLAST [Internet]. Bethesda (Md.): National Library of Medicine (US), National Center for Biotechnology Information; 2004-Apr. 11, 2018, available from: blast.ncbi.nlm.nih.gov) using GENBANK® Accession Nos. NP_001172085.1 (SEQ ID NO: 1) and NP_444325.2 (SEQ ID NO: 2), both incorporated by reference as available on Apr. 19, 2017.

SEQUENCE LISTING

Figures 2A, 2B:
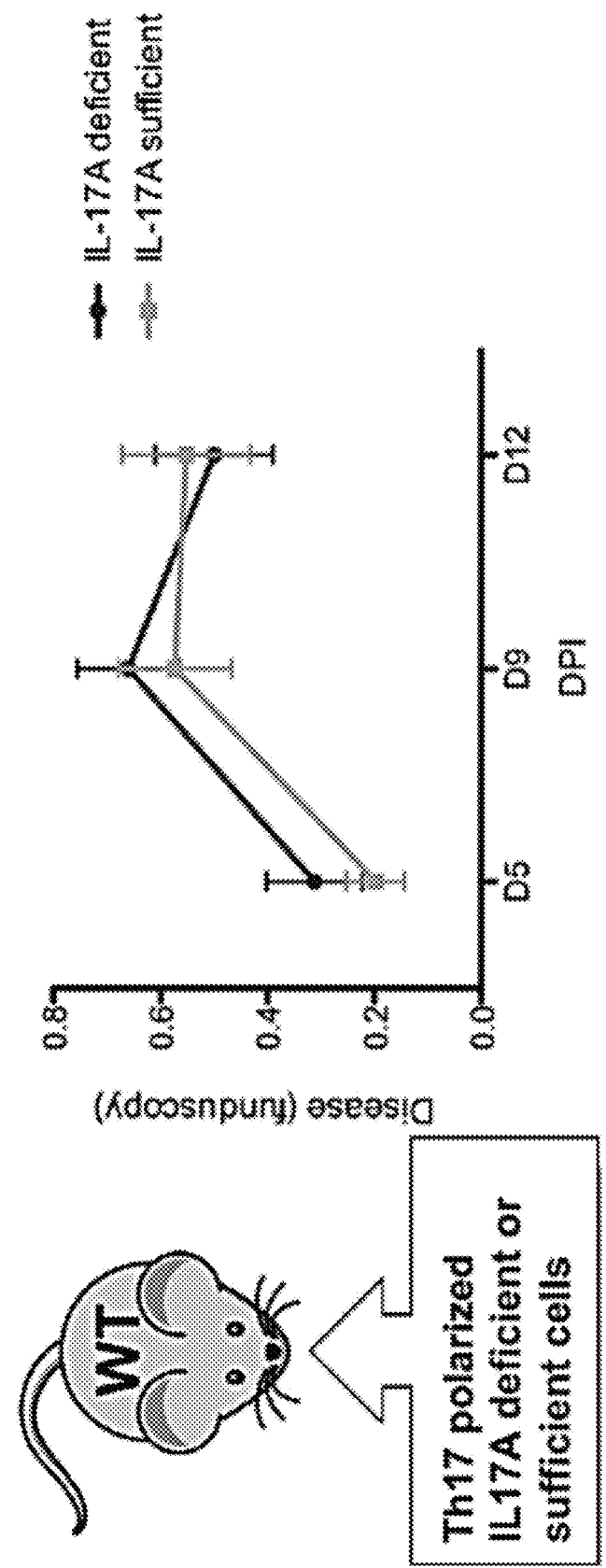
FIGS. 2A-2B show that IL-17A-deficient cells (circles) have an undiminished ability to induce experimental autoimmune uveitis (EAU) compared with and IL-17A-sufficient Th17 cells (squares).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Apr. 19, 2018, 6.7 KB, which is incorporated by reference herein. In the accompanying sequence listing:

SEQ ID NO: 1 is an exemplary human IL-24 protein sequence.

SEQ ID NO: 2 is an exemplary mouse IL-24 protein sequence.

SEQ ID NO: 3 is an exemplary human IL-24 nucleic acid sequence.

SEQ ID NOS: 4 and 5 are exemplary mouse IL-24 nucleic acid sequences.

DETAILED DESCRIPTION

Disclosed herein are methods for treating a subject with uveitis and/or ocular surface inflammation. The methods can include administering to the subject a therapeutically effective amount of an interleukin 24 (IL-24) polypeptide, or a nucleic acid encoding the IL-24 polypeptide, thereby treating the ocular surface inflammation and/or uveitis. In some examples, the administered IL-24 polypeptide suppresses production of effector cytokines by Th17 cells. In some embodiments, the IL-24 polypeptide is a variant of IL-24. In other examples, the IL-24 polypeptide is an Fc fusion protein that includes IL-24. The subject can be any mammal, such as a human. The ocular surface inflammation and/or uveitis can include a Th17 response.

In some non-limiting examples, the methods can include administering a therapeutically effective amount of a polypeptide at least 95% identical to the amino acid sequence of SEQ ID NO: 1 or a nucleic acid encoding this polypeptide. In other examples, the method includes administering to the subject a therapeutically effective amount of a polypeptide including the amino acid sequence of SEQ ID NO: 1 or a nucleic acid molecule encoding this polypeptide.

In some embodiments, any of the disclosed methods are used to treat uveitis. Thus, the method can include selecting a subject with uveitis. In some non-limiting examples, the uveitis is anterior uveitis, intermediate uveitis, posterior uveitis, or diffuse uveitis. In other non-limiting examples, the uveitis includes iritis, cyclitis, cyclitis, pars planitis, chorioretinitis, iridocyclitis, and/or iritis. In further non-limiting examples, the uveitis results from surgery, trauma, an autoimmune disorder, exposure to chemical stimuli, an infection, an inflammatory disorder, or the human leukocyte antigen B27 (HLA-B27) haplotype. In yet other non-limiting examples, the subject has an autoimmune disorder, such as sarcoidosis, ankylosing spondylitis, arthritis, multiple sclerosis, or psoriasis. In some non-limiting examples, the subject has an inflammatory disorder, such as uveitis associated with Crohn's disease, ulcerative colitis, or Behcet's syndrome. In other non-limiting examples, the subject has an infection, such as an the infection that results from cat-scratch disease, herpes zoster, herpes simplex, leptospirosis, toxocariasis, toxoplasmosis, syphilis, tuberculosis, Lyme disease, West Nile virus, cytomegalovirus, or human immunodeficiency virus (HIV). In yet other non-limiting examples, the subject has the haplotype HLA-B27.

In some embodiments, any of the disclosed methods are used to treat ocular surface disease. Thus, the method includes selecting a subject with the ocular surface disease, such as inflammation of the surface of the eye, such as the cornea, sclera, conjunctiva, or the tear ducts which connect to them as well as the eyelids. In some non-limiting examples, the subject has kertatitis, such as bacterial keratitis or viral keratitis. In further non-limiting examples, the keratitis results from laser eye therapy, trauma, exposure to ultraviolet light, exposure to chemical stimuli, contact lens wear, corneal transplant, or exposure to a toxin. In some examples, the keratitis is ulcerative. In some examples, the subject has Sjögren's syndrome.

In further embodiments, for the treatment of uveitis and/or an ocular surface disease, the methods further include administering a therapeutically effective amount of at least one of an additional anti-inflammatory agent, immunosuppressive agent, antibacterial agent, antifungal agent, or an immunomodulatory agent. In some examples, the additional agent administered is a glucocorticoid or calcineurin antagonist.

In some non-limiting examples, the polypeptide or the nucleic acid molecule is administered topically to the eye of the subject. In some examples, the polypeptide or the nucleic acid molecule is formulated in an ointment or solution for administration to the eye.

Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GENBANK® Accession Nos. referred to herein are the sequences available at least as early as Apr. 19, 2018. All references and GENBANK® Accession numbers cited herein are incorporated by reference as available on Apr. 19, 2017.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various embodiments of the disclosure, the following explanations of specific terms are provided.

Adeno-associated Virus (AAV): AAV is a small virus that infects humans and some other primate species. AAV is not currently known to cause disease and consequently the virus causes a very mild immune response. AAV can infect both dividing and non-dividing cells and mainly exists as episomal forms in the host cell. The AAV genome is constructed of single-stranded deoxyribonucleic acid (ssDNA), either positive- or negative-sense, which is approximately 4.7 kilobases (kb) long. The genome comprises inverted terminal repeats (ITRs) at both ends of the DNA strand and two open reading frames (ORFs): rep and cap. Rep is composed of four overlapping genes encoding Rep proteins required for the AAV life cycle, and Cap contains overlapping nucleotide sequences of capsid proteins: VP1, VP2 and VP3, which interact together to form a capsid of an icosahedral symmetry. For gene therapy, ITRs seem to be the only sequences required in cis next to the therapeutic gene: structural (cap) and packaging (rep) genes can be delivered in trans.

Agent: Any substance or any combination of substances that is useful for achieving an end or result. Agents include proteins, nucleic acid molecules, compounds, small molecules, organic compounds, inorganic compounds, or other molecules of interest. An agent can include a therapeutic agent, a diagnostic agent, or a pharmaceutical agent. Exemplary agents include anti-inflammatory, immunosuppressive, antibacterial, antifungal, and immunomodulatory agents as well as agents that increase the half-life of a co-administered molecule, such as an antibody with specificity for a co-administered protein or polypeptide (see, e.g., Webster et al., J Exp Med., 206(4): 751-760, 2009; Courtney et al., Immunopharmacology, 28(3):223-32, 1994).

Antibody: A polypeptide substantially encoded by an immunoglobulin gene or immunoglobulin genes or fragments thereof, which specifically binds (i.e., binds substantially or preferentially only to a defined target, such as to an antigen or analyte) and recognizes an analyte (i.e., an antigen, which is a polypeptide that can stimulate the production of antibodies or a T cell response in an animal, including polypeptides that are injected or absorbed into an animal). Immunoglobulin genes include the kappa, lambda, alpha, gamma, delta, epsilon, and mu constant region genes as well as myriad immunoglobulin variable region genes.

Antibodies exist, for example, as intact immunoglobulins and as a number of well-characterized fragments produced by digestion with various peptidases, such as Fabs, Fvs, and single-chain Fvs (SCFvs). Included are intact immunoglobulins as well as the variants and portions thereof that are well known in the art, such as Fab' fragments, F(ab)$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while, in dsFvs, the chains have been mutated to introduce a disulfide bond to stabilize the association of the chains. The term also includes genetically engineered forms, such as chimeric antibodies (e.g., humanized murine antibodies) and heteroconjugate antibodies (e.g., bispecific antibodies). See also, Pierce Catalog and Handbook, 1994-1995 (Pierce Chemical Co., Rockford, Ill.); Kuby, J., Immunology, 3 rd Ed., W.H. Freeman & Co., New York, 1997.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies. In some examples, monoclonal antibodies are isolated from a subject. The amino acid sequences of such isolated monoclonal antibodies can be determined.

A "polyclonal antibody" is an antibody that is secreted by different B cell lineages within the body (whereas monoclonal antibodies come from a single cell lineage). It includes a collection of immunoglobulin molecules that react against a specific antigen, each identifying a different epitope.

Autoimmune disorder: A disorder in which the immune system produces an immune response (e.g., a B cell or a T cell response) against an endogenous antigen, with consequent injury to tissues. For example, rheumatoid arthritis is an autoimmune disorder, as are Hashimoto's thyroiditis, pernicious anemia, Addison's disease, type I diabetes, Sjogren's syndrome, dermatomyositis, lupus erythematosus, multiple sclerosis, myasthenia gravis, Reiter's syndrome, and Grave's disease, among others.

Cornea: The transparent front part of the eye that covers the iris, pupil, and anterior chamber. Together with the lens, the cornea refracts light, and as a result helps the eye to focus, accounting for approximately two-thirds of the eye's total optical power. The cornea has unmyelinated nerve endings sensitive to touch, temperature and chemicals; a touch of the cornea causes an involuntary reflex to close the eyelid. The cornea does not have blood vessels; it receives nutrients via diffusion from the tear fluid at the outside and the aqueous humor at the inside and also from neurotrophins supplied by nerve fibers that innervate it. In humans, the cornea has a diameter of about 11.5 mm and a thickness of about 0.5-0.6 mm in the center and about 0.6-0.8 mm at the periphery. The cornea has five layers; from the anterior to posterior these layers are the corneal epithelium, Bowman's layer, the corneal stroma, Descemet's membrane, and the corneal endothelium.

Conjunctivitis: Inflammation of the conjunctiva, which lines the inside of the eyelids and covers the sclera. The conjunctiva is composed of non-keratinized stratified columnar epithelium with goblet cells. There are many types of conjunctivitis, including allergic conjunctivitis, bacterial conjunctivitis, viral conjunctivitis, and chemical conjunctivitis. Generally in conjunctivitis the eye appears red, but the pupils are normally reactive to light and visual acuity is unchanged.

Non-limiting example of a conjunctivitis are viral conjunctivitis, bacterial conjunctivitis, fungal conjunctivitis, parasitic conjunctivitis, or allergic conjunctivitis. Acute conjunctival inflammation is conjunctival inflammation that generally occurs for less than two weeks, 1, 2, 3, 4, 5, 6, 7, 8, 9, 10 11, 12 or 13 days or less. Chronic conjunctival inflammation is conjunctival inflammation that occurs for at least two weeks such as for 3, 4, 5, 6, 7, 8, 9, 10 weeks or more, such as for months or years.

Conjunctivitis is characterized by presence or observation of two or more (e.g., three, four, or five) of the following in a subject: an elevated number of T-lymphocytes (e.g., effector T cells) in a conjunctiva, an elevated number of dendritic cells in a conjunctiva, an elevated number of macrophages in a conjunctiva, an elevated number of stimulated monocytes in a conjunctiva, an elevated number of natural killer cells in a conjunctiva, an elevated number of B-cells in a conjunctiva, an elevated number of eosinophils in a conjunctiva, an elevated number of mast cells in a conjunctiva, an elevated level of redness in a white of an eye or inner eyelid, pain in an eye, irritation, itchiness, burning, and/or dryness of an eye, excess tears or other discharge from an eye, difficulty opening an eyelid, blurred vision, sensitivity to light, and swelling around an eye (e.g., as compared to the levels in the same subject prior to conjunctival inflammation, a subject not having an eye disorder (a healthy subject), or a threshold value).

The detection of an elevated level of the number of immunological cells present in the conjunctiva can be accomplished using methods known in the art, such as in vivo confocal microscopy (see, e.g., Cruzat et al, Semin. Ophthalmol. 25: 171-177, 2010).

Conservative variants: "Conservative" amino acid substitutions are those substitutions that do not substantially affect or decrease an activity or antigenicity of an antigenic epitope of Brachyury. Specific, non-limiting examples of a conservative substitution include the following examples:

| Original Residue | Conservative Substitutions |
|---|---|
| Al | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variant also includes the use of a substituted amino acid in place of an unsubstituted parent amino acid, provided that antibodies raised to the substituted polypeptide also immunoreact with the unsubstituted polypeptide, and/or that the substituted polypeptide retains the function of the unsubstituted polypeptide. Non-conservative substitutions are those that reduce an activity or antigenicity.

Cytokine: Proteins made by cells that affect the behavior of other cells, such as lymphocytes. In one embodiment, a cytokine is a chemokine, a molecule that affects cellular trafficking. In another embodiment, a cytokine alters the maturation of lymphocytes, and influences isotype switching by B cells.

Dry eye: A condition that occurs when either the eye does not produce enough tears or when the tears evaporate too quickly. This can result from meibomian gland dysfunction, allergies, pregnancy, Sjogren's syndrome, vitamin A deficiency, LASIK surgery, and certain medications such as antihistamines, some blood pressure medication, hormone replacement therapy, and antidepressants. Chronic conjunctivitis such as from tobacco smoke exposure or infection may also lead to the condition. Diagnosis is based on symptoms, evaluation of tear secretion, and/or staining of the ocular surface.

Dry eye syndrome (DES): Also known as dry eye disease (DED), keratoconjunctivitis sicca (KCS), and keratitis sicca, DES is a multifactorial disease of the tears and the ocular surface that results in discomfort, visual disturbance, and tear film instability with potential damage to the ocular surface. Dry eye syndrome is a common form of ocular surface disease (OSD) and may overlap with other causes of OSD, such as ocular allergy and meibomian gland dysfunction (MGD).

Excipient: Any pharmaceutical agent that does not itself induce the production of antibodies harmful to a subject receiving a composition and that may be administered without undue toxicity. Pharmaceutically acceptable excipients include, but are not limited to, liquids such as water, saline, glycerol, and ethanol. In some examples, excipients can include agents that release a pharmaceutical composition as it degrades, thus modulating the release of the composition (i.e., increasing or decreasing the rate and/or stabilizing the composition).

Experimental autoimmune uveoretinitis (EAU): An animal model for uveitis that can be induced by several retinal autoantigens (see Gery and Streilein, *Curr. Opinion Immunol.* 6:938, 1994; Nussenblatt and Gery, *J. Autoimmunity* 9:575-585, 1996; Gery et al., "Autoimmune Diseases of the Eye. In: Theofilopoulosand Bona" (eds.), *The Molecular Pathology of Autoimmune Diseases,* 2nd Edition, Taylor and Francis, New York, pp. 978-998, 2002). Generally, intraocular inflammation is induced in a non-human animal species using an autoantigen. For example, immunization of a mouse, rat, rabbit or pig with an ocular-specific antigen can be used to produce the model system. Both arrestin and interphotoreceptor retinol protein (IRBP, for amino acid sequences see Swissprot Accession Nos. P12661, P49194, P12662) have been used to produce EAU.

One of the most evaluated antigen and model systems is EAU induced by the retinal S-antigen (S—Ag, see Swissprot Accession Nos. Q99858, P10523, P20443, P36576). S—Ag binds phosphorylated cytopigments and blocks the interaction of transducin with the photoexcited light receptor of the visual cascade. S—Ag is the only retinal autoantigen to which a substantial number of human patients with endogenous intermediate and posterior uveitis consistently demonstrate in vitro proliferative responses (Nussenblatt et al., *Am. J. Ophthalmol.* 89:173, 1980; Nussenblatt et al., *Am. J. Ophthalmol.* 94:147, 1982). The entire amino acid sequence of S—Ag has been described, with two fragments designated N and M, respectively, demonstrating uveitogenicity (Donoso et al., *Curr. Eye Res.* 8:1151, 1987; Singh et al., *Cell. Immunol.* 115:413, 1988) Immune manipulation of this model appears to have excellent predictive value for the human uveoretinitis, as was demonstrated with the clinical effectiveness of cyclosporine use in humans (Nussenblatt et al., *J. Clin. Invest.* 67:1228, 1981) which was first tested on the EAU model.

Eye disease: Includes external eye disease and intraocular eye disease. Examples of external eye disease include disease associated with the cornea and eyelid. Intraocular disease includes uveitis, such as iritis, cyclitis, panuveitis, posterior uveitis, and anterior uveitis. Diseases of the eyelid (e.g., meibomian gland dysfunction (MGD) and anterior blepharitis) can cause corneal surface disease, such as dry eye and keratitis.

Fc polypeptide: The polypeptide comprising the constant region of an antibody excluding the first constant region immunoglobulin domain. The Fc region generally refers to the last two constant region immunoglobulin domains of IgA, IgD, and IgG as well as the last three constant region immunoglobulin domains of IgE and IgM. An Fc region may also include part or all of the flexible hinge N-terminal to these domains. For IgA and IgM, an Fc region may or may not comprise the tailpiece and may or may not be bound by the J chain. For IgG, the Fc region comprises immunoglobulin domains Cgamma2 and Cgamma3 (C$\gamma$2 and C$\gamma$3) and the lower part of the hinge between Cgamma1 (C$\gamma$1) and C$\gamma$2. Although the boundaries of the Fc region may vary, the human IgG heavy chain Fc region typically includes residues C226 or P230 through the carboxyl-terminus, wherein the numbering is according to the EU index as in Kabat. For IgA, the Fc region comprises immunoglobulin domains Calpha2 and Calpha3 (C$\alpha$2 and C$\alpha$3) and the lower part of the hinge between Calpha1 (C$\alpha$1) and C$\alpha$2.

Encompassed within the definition of the Fc region are functionally equivalent analogs and variants of the Fc region. A functionally equivalent analog of the Fc region may be a variant Fc region, comprising one or more amino acid modifications relative to the wild-type or naturally existing Fc region. Variant Fc regions will possess at least 50% homology with a naturally existing Fc region, such as about 80% or about 90% or at least about 95% homology. Functionally equivalent analogs of the Fc region may comprise one or more amino acid residues added to or deleted from the N- or C-termini of the protein, such as no more than 30 or no more than 10 additions and/or deletions. Functionally equivalent analogs of the Fc region include Fc regions operably linked to a fusion partner. Functionally equivalent analogs of the Fc region must comprise the majority of all of the Ig domains that compose the Fc region as defined above. The Fc region may refer to this region in isolation, or this region in the context of a fusion protein.

Fusion protein: Proteins that have at least two domains fused together. In general, the domains of the disclosed fusions are genetically fused together, in that, nucleic acid molecules that encode each protein domain (or subdomain) are functionally linked together, such as directly or through a linker oligonucleotide, thereby producing a fusion protein-encoding (chimeric) nucleic acid molecule. The translated product of such a fusion-encoding (chimeric) nucleic acid molecule is the fusion protein (e.g., a fusion protein that includes an Fc polypeptide linked to IL-24, i.e., an "Fc fusion protein").

Half-life: A measurement of decay time for discrete molecules or of decay for activity of a substance. The half-life is the time required for half of a given amount of molecules to decay, for a substance to lose half of its activity, or for the concentration of a substance to reach half of its steady-state value.

Interleukin 17A (IL-17A or IL-17): Also known as cytotoxic T-lymphocyte-associated serine esterase 8 (CTLA8; e.g., OMIM 603149), IL-17A is a proinflammatory cytokine primarily secreted by activated T cells. IL-17 simulates a variety of cells to produce inflammatory mediators, including IL-1, TNF$\alpha$, and chemokines, ultimately leading to neutrophil and leukocyte recruitment, the hallmark of inflammatory disease.

Includes IL-17A nucleic acid molecules and proteins. IL-17A sequences are publicly available. For example, GENBANK® Accession Nos. NM_002190.2, NM_001106897.1, and NM_010552.3 disclose exemplary human, rat, and mouse IL-17A nucleotide sequences, respectively, and GENBANK® Accession Nos. AAH67505.1, NP_001100367.1, and NP_034682.1 disclose exemplary human, rat, and mouse IL-17A protein sequences, respectively. One of ordinary skill in the art can identify additional IL-17A nucleic acid and protein sequences, including IL-17A variants that retain IL-17A biological activity.

Interleukin 24 (IL-24): Also known as suppression of tumorigenicity 16 (ST16) and melanoma differentiation-associated gene 7 (MDA7), IL-24 is a cytokine in the IL-10 family of cytokines and controls cell survival and proliferation by inducing rapid activation of transcription factors. IL-24 is released by activated monocytes, macrophages, and T helper 2 (Th2) cells and acts on non-haematopoietic tissues, such as skin, lung, and reproductive tissues with an important role in wound healing, arthritis, psoriasis, and cancer.

An "IL-24 polypeptide" includes fusion proteins that include IL-24 and variants of IL-24. IL-24 sequences are publicly available. For example, GENBANK® Accession Nos. LQ620259.1, NM_133311.1, and LQ620261.1 disclose exemplary human, rat, and mouse IL-24 nucleotide sequences, respectively, and GENBANK® Accession Nos. AAH09681.1, NP_579845.1, and NP_444325.2 disclose exemplary human, rat, and mouse IL-24 protein sequences, respectively. One of ordinary skill in the art can identify additional IL-24 nucleic acid and protein sequences, including IL-24 variants that retain IL-24 biological activity (such as treating ocular inflammation).

Immunosuppressive agent: A molecule, such as a chemical compound, small molecule, steroid, nucleic acid molecule, or other biological agent, that can decrease an immune response such as an inflammatory reaction Immunosuppressive agents include, but are not limited to an agent of use in treating uveitis and/or ocular surface inflammation. Specific, non-limiting examples of immunosuppressive agents are corticosteroids, cyclosporine A, FK506, and anti-CD4. In additional examples, the agent is a biological response modifier, such as KINERET® (anakinra), ENBREL® (etanercept), or REMICADE® (infliximab), a disease-modifying antirheumatic drug (DMARD), such as ARAVA® (leflunomide). Agents of use to treat inflammation include non-steroidal anti-inflammatory drugs (NSAIDs), specifically a Cyclo-Oxygenase-2 (COX-2) inhibitor, such as CELEBREX® (celecoxib) and VIOXX® (rofecoxib), or another product, such as HYALGAN® (hyaluronan) and SYNVISC® (hylan G-F20).

Immune response: A response of a cell of the immune system, such as a B cell, T cell, or macrophage, to a stimulus. In one embodiment, the response is specific for a particular antigen (an "antigen-specific response").

Inflammation: The complex biological response of body tissues to harmful stimuli, such as pathogens, damaged cells, or irritants, and is a protective response involving immune cells, blood vessels, and molecular mediators. The function of inflammation is to eliminate the initial cause of cell injury, clear out necrotic cells and tissues damaged from the original insult and the inflammatory process, and to initiate tissue repair.

The classical signs of acute inflammation are calor, dolor, rubor, tumor (heat, pain, redness and swelling) and loss of function. Inflammation is a generic response, and therefore it is considered a mechanism of innate immunity, in contrast to adaptive immunity, which is specific for each pathogen. Prolonged inflammation, known as "chronic inflammation," leads to a progressive shift in the type of cells present at the site of inflammation, such as mononuclear cells, and is characterized by simultaneous destruction and healing of the tissue from the inflammatory process. "Ocular inflammation" is inflammation of the eye.

Infectious agent: An agent that can infect a subject, including, but not limited to, viruses, bacteria and fungi.

Inhibiting or treating a disease: Inhibiting the full development of a disease or condition, for example, in a subject who is at risk for a disease such as uveitis and/or ocular surface inflammation. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component has been substantially separated, produced apart from, or purified away from other biological components in the cell of the organism in which the component naturally occurs, such as, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides, and proteins prepared by recombinant expression in a host cell as well as chemically synthesized nucleic acids.

Liposome: A spherical vesicle having at least one lipid bilayer. The liposome can be used as a vehicle for administration of nutrients and pharmaceutical drugs. Liposomes can be prepared by disrupting biological membranes (such as by sonication). Liposomes can be composed of phospholipids, especially phosphatidylcholine, but may also include other lipids, such as egg phosphatidylethanolamine, compatible with the lipid bilayer structure. A liposome design may employ surface ligands for attaching to unhealthy tissue. Exemplary liposomes include multilamellar vesicles (which include several lamellar phase lipid bilayers), small unilamellar liposome vesicles (which can include one lipid bilayer), large unilamellar vesicles, cochleate vesicles, and multivesicular liposomes (in which one vesicle contains one or more smaller vesicles).

Keratitis: An inflammation or irritation of the cornea. Typical symptoms include red eye, foreign body sensation, pain, sensitivity to light, watery eyes, and blurred vision. Keratitis is the most common cause of corneal blindness caused by infection in the United States. It can be caused by injury to the cornea, dryness and/or inflammation of the ocular surface, and infectious agents, such as herpes zoster and herpes simplex, and bacterial infections, such as *Staphylococcus aureus* and *Pseudomonas aeruginosa*. There are other forms of keratitis, such as exposure keratitis, photokeratitis caused by exposure to ultraviolet radiation, and allergic keratitis. Keratitis also can be caused by fungal infections (such as by *Fusarium*) and amoebic infections (*Acanthamoeba*). Infectious keratitis can progress rapidly, and generally requires urgent antibacterial, antifungal, or antiviral therapy to eliminate the pathogen. However, the underlying inflammation can cause persistent corneal injury (such as a scar) even after the infection or corneal trauma has been successfully treated. Corticosteroids are sometimes used to treat such inflammation but they can have undesired side effects such as increased intraocular pressure.

Superficial keratitis involves the superficial layers (the epithelium) of the cornea. Deep keratitis involves deeper layers of the cornea (including the epithelium, Bowman's Membrane and often the stroma).

Acute corneal inflammation is corneal inflammation that generally occurs for less than two weeks, such as 1, 2, 3, 4, 5, 6, 7, 8, 9, 10 11, 12 or 13 days or less. Chronic corneal inflammation is corneal inflammation that occurs for at least two weeks, such as for 3, 4, 5, 6, 7, 8, 9, 10 weeks or more, such as for months or years.

In keratitis, the presence of two or more (e.g., three, four, or five) of the following is observed in a subject: an elevated number of T-lymphocytes (e.g., effector T cells) in a cornea, an elevated number of dendritic cells in a cornea, an elevated number of macrophages in a cornea, an elevated number of eosinophils in a cornea, an elevated number of mast cells in a cornea, an elevated number of B-cells in a cornea, an elevated number of stimulated monocytes in a cornea, an elevated number of natural killer cells in a cornea, an elevated level of redness in a cornea, pain in an eye, irritation, itchiness, burning, and/or dryness of a cornea, excess tears or other discharge from an eye, difficulty opening an eyelid, blurred vision, sensitivity to light, and swelling around the eye (e.g., as compared to the levels in the same subject prior to corneal inflammation, a subject not having an eye disorder (a healthy subject), or a threshold value). The detection of an elevated level of the number of immunological cells present in the cornea can be accomplished using methods known in the art, such as in vivo confocal microscopy (see, e.g., Cruzat et al., Semin Ophthalmol. 25: 171-177, 2010). However, the existence of corneal inflammation also can be inferred from other underlying causes (such as trauma or infection) or the appearance of the eye (such as redness and tearing).

Mammal: This term includes both human and non-human mammals. Similarly, the term "subject" includes both human and veterinary subjects.

Ocular surface: The surface of the eye, including the cornea and conjunctiva.

Ocular surface disease: Ocular surface disease is a disorder of the corneal surface. The causes of ocular surface disease are multifactorial and can include such eye diseases as dry eye as well as non-dry eye conjunctivitis and keratitis (e.g., allergic conjunctivitis, infective and noninfective keratitis, and conjunctivitis). Even other forms of external eye inflammation can cause ocular surface disease, for example, inflammation associated with non-dry eye lid disease (e.g., meibomian gland dysfunction (MGD) and anterior blepharitis).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, intra-vitreously, or subcutaneously, and various surface applications including intranasal, intradermal, and topical application, for instance.

Pharmaceutical agent or drug: A chemical compound or composition capable of inducing a desired therapeutic or prophylactic effect when properly administered to a subject. Pharmaceutical agents include, but are not limited to, immunosuppressive agents.

Pharmaceutically acceptable carriers: The pharmaceutically acceptable carriers useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: A single- or double-strand ("ss" or "ds," respectively) polymer of deoxyribonucleotide or ribonucleotide bases read from the 5' to the 3' end. Polynucleotides include RNA and DNA and may be isolated from natural sources, synthesized in vitro, or prepared from a combination of natural and synthetic molecules. In some examples, two strands of a double-stranded polynucleotide may differ in length and that the ends thereof may be staggered as a result of hybridization or enzymatic cleavage; thus, all nucleotides within a double-stranded polynucleotide molecule may not be paired.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced.

The term "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Preventing or treating a disease: "Preventing" a disease refers to inhibiting the full development of a disease, for example in a person who is known to have a predisposition to a disease such as an autoimmune disorder. An example of a person with a known predisposition is someone with a history of a disease in the family, or who has been exposed to factors that predispose the subject to a condition. "Treatment" refers to a therapeutic intervention that ameliorates a sign or symptom of a disease or pathological condition after it has begun to develop.

Promoter: A promoter is an array of nucleic acid control sequences that directs transcription of a nucleic acid. A promoter includes necessary nucleic acid sequences near the start site of transcription, for example, in the case of a polymerase II type promoter, a TATA element. A promoter also optionally includes distal enhancer or repressor elements which can be located as much as several thousand base pairs from the start site of transcription. Both constitutive and inducible promoters are included (see, e.g., Bitter et al., Methods in Enzymology 153:516-544, 1987).

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well-known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988, Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well-known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=-4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

Sjögren's syndrome: A disorder of the immune system, which is identified by its two most common symptoms, dry eyes and a dry mouth. Sjogren's syndrome often accompanies other immune system disorders, such as rheumatoid arthritis and lupus. In Sjogren's syndrome, the mucous membranes and moisture-secreting glands of your eyes and mouth are usually affected first, resulting in decreased production of tears and saliva.

Subject: As used herein, the term "subject" refers to a mammal and includes, without limitation, humans, domestic animals (e.g., dogs or cats), farm animals (e.g., cows, horses, or pigs), non-human primates, and laboratory animals (mice, rats, hamsters, guinea pigs, pigs, rabbits, dogs, or monkeys).

T cells: Also known as T lymphocytes, a T cell is a type of lymphocyte (a white blood cell subtype) that is involved in cell-mediated immunity with a characteristic T cell receptor on the cell surface. T cell types include effector T cells that actively respond to a stimulus, such as helper T cells (Th cells), which differentiate into a specific subtype upon activation and secrete characteristic cytokines to facilitate a particular type of immune response.

T helper 17 cells (Th17 cells): Th17 cells are pro-inflammatory T helper cells defined by their production of interleukin 17 (IL-17). Th17 cells aid in maintaining mucosal barriers, and they play a role in autoimmune and inflammatory disorders as well as adaptive immunity. Loss of Th17 cell populations can lead to chronic inflammation and microbial translocation. The main effector cytokines (i.e., cytokines primarily secreted by the differentiated or polarized Th17 cells) are IL-17A, IL-17F, IL-21, and IL-22. Th17 cells can mediate tumor regression or tumor formation through inflammation. Th17 cells closely interact with B cells and are involved in their recruitment, and Th17 cells can encourage antibody production. Th17 cell dysregulation is associated with autoimmune disorders, such as rheumatoid arthritis, inflammation, and infection.

Th17 cells differentiate or are polarized from naïve T cells in the presence of several cytokines, including transforming growth factor-β (TGF-β), IL-1β, IL-6, IL-21, and IL-23 in mice and humans, which also known as a "Th17 response." Th17 cell pro-inflammatory activity can be beneficial to a host during infection. However, an uncontrolled response or inappropriate Th17 activation is linked to several autoimmune and autoinflammatory pathologies; Th17 cells are associated with several autoimmune diseases, such as arthritis, multiple sclerosis, psoriasis, and lupus.

Therapeutic agent: Used in a generic sense, it includes treating agents, prophylactic agents, and replacement agents.

Therapeutically effective amount: A quantity of an agent sufficient to achieve a desired effect in a subject being treated. For instance, this can be the amount of a IL-24 polypeptide or a polynucleotide encoding this polypeptide necessary to treat uveitis or ocular inflammation in a subject, or a dose sufficient to prevent advancement, or to cause regression of a disease, such as uveitis, or which is capable of relieving symptoms caused by a disease, such as ocular inflammation. In one example, the amount is sufficient to prevent advancement, or to cause regression of the disease. In another example, the amount is sufficient to inhibit a sign or symptom of uveitis, such as the presence of inflammatory cells in the anterior chamber of the eye or spasm of the ciliary body, or to reduce lymphocyte infiltration.

An effective amount of an IL-24 polypeptide or a nucleic acid encoding an IL-24 polypeptide can be administered systemically or locally (see below). In addition, an effective amount can be administered in a single dose, or in several doses, for example daily, during a course of treatment. However, the effective amount will be dependent on the preparation applied, the subject being treated, the severity and type of the affliction, and the manner of administration of the compound The methods disclosed herein have equal applications in medical and veterinary settings. Therefore, the general terms "subject" and "subject being treated" are understood to include all animals, including humans or other simians, dogs, cats, horses, and cows.

Uveitis: An intraocular inflammatory disease that includes iritis, cyclitis, panuveitis, posterior uveitis, and anterior uveitis. Iritis is inflammation of the iris. Cyclitis is inflammation of the ciliary body. Panuveitis refers to inflammation of the entire uveal (vascular) layer of the eye. Intermediate uveitis, also called peripheral uveitis, is centered in the area immediately behind the iris and lens in the region of the ciliary body and pars plana, and is also termed "cyclitis" and "pars planitis."

"Posterior" uveitis generally refers to chorioretinitis (inflammation of the choroid and retina). Posterior uveitis can give rise to diverse symptoms but most commonly causes floaters and decreased vision similar to intermediate uveitis. Signs include cells in the vitreous humor, white or yellow-white lesions in the retina and/or underlying choroid, exudative retinal detachments, retinal vasculitis, and optic nerve edema.

Anterior uveitis refers to iridocyclitis (inflammation of the iris and the ciliary body) and/or iritis. Anterior uveitis tends to be the most symptomatic, typically presenting with pain, redness, photophobia, and decreased vision. Signs of anterior uveitis include pupillary miosis and injections of the conjunctiva adjacent to the cornea, so-called perilimbal flush. Biomicroscopic, or slit lamp, findings include cells and flare in the aqueous humor as well as keratic precipitates, which are clumps of cells and proteinaceous material adherent to the corneal endothelium. "Diffuse" uveitis implies inflammation involving all parts of the eye, including anterior, intermediate, and posterior structures.

"Acute" uveitis is a form of uveitis in which signs and symptoms occur suddenly and last for up to about six weeks. "Chronic" uveitis is a form in which onset is gradual and lasts longer than about six weeks.

The inflammatory products (i.e., cells, fibrin, excess proteins) of ocular inflammation are commonly found in the fluid spaces of the eye, i.e., anterior chamber, posterior chamber and vitreous space as well as infiltrating the tissue imminently involved in the inflammatory response.

Uveitis may occur following surgical or traumatic injury to the eye; as a component of an autoimmune disorder (such as rheumatoid arthritis, Bechet's disease, ankylosing spondylitis, sarcoidosis); as an isolated immune mediated ocular disorder (such as pars planitis or iridocyclitis); as a disease unassociated with known etiologies, and following certain systemic diseases which cause antibody-antigen complexes to be deposited in the uveal tissues. Uveitis includes ocular inflammation associated with Bechet's disease, sarcoidosis, Vogt-Koyanagi-Harada syndrome, birdshot chorioretinopathy and sympathetic ophthalmia. Thus, non-infectious uveitis occurs in the absence of an infectious agent.

A wide variety of infective agents can also cause uveitis. When an infective etiology has been diagnosed, an appropriate antimicrobial drug can be given to cure the disease. Certain cancers are also associated with uveitis, including lymphoma and ocular malignant melanoma. However, the etiology of uveitis remains elusive in the majority of cases.

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like. A vector can be a viral vector.

Overview

Provided herein are methods for treating uveitis and/or ocular surface inflammation, including such inflammation associated with uveitis and/or ocular surface disease. A therapeutically effective amount of IL-24 polypeptides and/or polynucleotides encoding IL-24 polypeptides can be administered to treat the ocular surface inflammation.

It is known that uveitogenic Th17 effector cells are controlled by IFN-γ and by IL-27, generated through an innate positive feedback loop, which limits their generation and induces Tr1 cells that inhibit their function. Without being bound by theory, Th17 cells cause tissue damage by producing a stereotypic profile of pro-inflammatory cytokines, including IL-17A, IL-17F, granulocyte macrophage colony-stimulating factor (GM-CSF), and IL-22.

It is disclosed herein that injection of IL-17 ameliorates EAU. This result is unexpected because the Th17 response and IL-17A are associated with autoimmune diseases and IL-17A-producing T cells are pathogenic effectors in models of autoimmunity, including experimental autoimmune uveitis (EAU). In a mouse model of spontaneous uveitis that expresses a transgenic interstitial retinol-binding protein (IRBP)-specific T cell receptor, IL-17A deficiency does not reduce uveitis severity. Other Th1-related cytokines (e.g., IL-17F, IL-22, and GM-CSF, in Th17 cells) compensate for the loss of "pathogenic" IL-17A, which is reversed by recombinant (r) IL-17A. However, gene expression profiling shows lower IL-24 expression in Th17 cells in association with IL-17A deficiency, and IL-24 suppressed production of effector cytokines by Th17 cells and inhibits their ability to induce EAU.

IL-24 Polypeptides and Polynucleotides Encoding IL-24

Human and mouse IL-24 polypeptides and polynucleotides are disclosed in Patent Publication No. WO2016174153 A1, incorporated herein by reference. IL-24 polypeptides and polynucleotides encoding an IL-24 polypeptide, are of use in the disclosed methods, wherein the IL-24 polypeptide suppresses production of effector cytokines by Th17 cells. In some examples, the effector cytokines are IL-17A, IL-17F, IL-21, and/or IL-22.

These methods disclosed herein utilize IL-24 polypeptides and/or nucleic acids that encode IL-24 polypeptides.

An exemplary human IL-24 is:

MNFQQRLQSLWTLASRPFCPPLLATASQMQMVVLPCLGFTLLLWSQVSGA

QGQEFHFGPCQVKGVVPQKLWEAFWAVKDTMQAQDNITSARLLQQEVLQN

VSDAESCYLVHTLLEFYLKTVFKNYHNRTVEVRTLKSFSTLANNFVLIVS

QLQPSQENEMFSIRDSAHRRFLLFRRAFKQLDVEAALTKALGEVDILLTW

MQKFYKL (SEQ ID NO: 1, see GENBANK Accession Nos.

NP_001172085.1 and AAH09681.1, both of which are incorporated herein by reference).

An exemplary mouse IL-24 is:

MLTEPAQLFVHKKNQPPSHSSLRLHFRTLAGALALSSTQMSWGLQILPCL

SLILLLWNQVPGLEGQEFRFGSCQVTGVVLPELWEAFWTVKNTVQTQDDI

TSIRLLKPQVLRNVSGAESCYLAHSLLKFYLNTVFKNYHSKIAKFKVLRS

FSTLANNFIVIMSQLQPSKDNSMLPISESAHQRFLLFRRAFKQLDTEVAL

VKAFGEVDILLTWMQKFYHL (SEQ ID NO: 2, see GENBANK

Accession No. NP_444325.2, incorporated herein by reference).

In some embodiments, the methods include administering variants of IL-24, such as polypeptides about 95%, 96%, 97%, 98%, or 99% identical to human or mouse IL-24. In some embodiments, an IL-24 polypeptide at least 95% identical to the amino acids set forth in SEQ ID NO: 1 or SEQ ID NO: 2 is administered, such as at least 95%, at least 96%, at least 97%, at least 98%, at least 99%, or 100% identical to the amino acid sequence of SEQ ID NO: 1 or SEQ ID NO: 2. In further embodiments, the IL-24 polypeptide administered includes at most 1, 2, 3, 4, 5, 6, 7, 8, 9, or 10 conservative substitutions in SEQ ID NO: 1 or at most 1, 2, 3, 4, 5, 6, 7, 8, 9, 10, or 11 conservative substitutions in SEQ ID NO: 2, wherein the polypeptide retains an anti-inflammatory activity, such as suppressing Th17 cell effector cytokines and/or inhibiting uveitis and/or ocular surface inflammation.

An Il-24 polypeptide can be included in a fusion protein. Thus, in some embodiments, Il-24 is administered as a fusion protein, such as an Fc fusion protein. In some specific, non-liming examples, the Fc domain is an IgG Fc domain, such as an $IgG_1$, $IgG_2$, $IgG_3$ or $IgG_4$ Fc domain. In some embodiments, these forms of Il-24 have an increased half-life as compared to the Il-24 not included in the fusion protein.

Without being bound by theory, the Fc domain increases the half-life of an IgG through its unique pH-dependent association with the neonatal Fc receptor (FcRn). After internalization, the Fc domain of IgG can bind to FcRn in the acidic environment of the endosome, so that the IgG is then cycled onto the cell surface and re-released into circulation. This biological system protects IgG from degradation and results in a long serum half-life. Fusions of an Fc domain and a therapeutic molecule have an extended half life. In addition, since the Fc fragment of IgG consists of a tightly packed homodimer, two therapeutic proteins are present in each molecule. Recently, monomeric Fc fusion proteins were generated in which a single active protein was fused to dimeric wild-type Fc. These smaller molecules have been shown to possess even extended half-lives compared with the dimeric version.

In some other examples, the method includes administering a nucleic acid molecule encoding the IL-24 polypeptide.

An exemplary nucleic acid encoding human IL-24 is:

ATGAATTTTCAACAGAGGCTGCAAAGCCTGTGGACTTTAGCCAGACCCTT

CTGCCCTCCTTTGCTGGCGACAGCCTCTCAAATGCAGATGGTTGTGCTCC

CTTGCCTGGGTTTTACCCTGCTTCTCTGGAGCCAGGTATCAGGGGCCCAG

GGCCAAGAATTCCACTTTGGGCCCTGCCAAGTGAAGGGGGTTGTTCCCCA

GAAACTGTGGGAAGCCTTCTGGGCTGTGAAAGACACTATGCAAGCTCAGG

ATAACATCACGAGTGCCCGGCTGCTGCAGCAGGAGGTTCTGCAGAACGTC

TCGGATGCTGAGAGCTGTTACCTTGTCCACACCCTGCTGGAGTTCTACTT

GAAAACTGTTTTCAAAAACTACCACAATAGAACAGTTGAAGTCAGGACTC

TGAAGTCATTCTCTACTCTGGCCAACAACTTTGTTCTCATCGTGTCACAA

CTGCAACCCAGTCAAGAAAATGAGATGTTTTCCATCAGAGACAGTGCACA

CAGGCGGTTTCTGCTATTCCGGAGAGCATTCAAACAGTTGGACGTAGAAG

CAGCTCTGACCAAAGCCCTTGGGGAAGTGGACATTCTTCTGACCTGGATG

-continued

CAGAAATTCTACAAGCTC (SEQ ID NO: 3, see GENBANK Accession No. LQ620259.1, incorporated herein by reference).

Exemplary nucleic acids encoding mouse IL-24 are:

ATGCTGACTGAGCCTGCCCAACTTTTTGTGCACAAGAAGAACCAGCCACC
TTCACACAGCAGCCTCCGGCTTCACTTTAGGACCCTAGCAGGAGCACTGG
CCCTTTCTTCAACACAGATGAGTTGGGGACTACAGATTCTCCCCTGCCTG
AGCCTAATCCTTCTTCTTTGGAACCAAGTGCCAGGGCTTGAGGGTCAAGA
GTTCCGATTTGGGTCTTGCCAAGTGACAGGGGTGGTTCTCCCAGAACTGT
GGGAGGCCTTCTGGACTGTGAAGAACACTGTGCAAACTCAGGATGACATC
ACAAGCATCCGGCTGTTGAAGCCGCAGGTTCTGCGGAATGTCTCGGGTGC
TGAGAGCTGTTACCTTGCCCACAGCCTGCTGAAGTTCTACTTGAACACTG
TTTTCAAGAACTACCACAGCAAAATAGCCAAATTCAAGGTCTTGAGGTCA
TTCTCCACTCTGGCCAACAACTTCATAGTCATCATGTCACAACTACAGCC
CAGTAAGGACAATTCCATGCTTCCCATTAGTGAGAGTGCACACCAGCGGT
TTTTGCTGTTCCGCAGAGCATTCAAACAGTTGGATACAGAAGTCGCTTTG
GTGAAAGCCTTTGGGGAAGTGGACATTCTCCTGACCTGGATGCAGAAATT
CTACCATCTC (SEQ ID NO: 4, see GENBANK Accession No. LQ620261.1, incorporated herein by reference).

GAAGCTTGCCACCATGCTGACTGAGCCTGCCCAACTTTTTGTGCACAAGA
AGAACCAGCCACCTTCACACAGCAGCCTCCGGCTTCACTTTAGGACCCTA
GCAGGAGCACTGGCCCTTTCTTCAACACAGATGAGTTGGGGACTACAGAT
TCTCCCCTGCCTGAGCCTAATCCTTCTTCTTTGGAACCAAGTGCCAGGGC
TTGAGGGTCAAGAGTTCCGATTTGGGTCTTGCCAAGTGACAGGGGTGGTT
CTCCCAGAACTGTGGGAGGCCTTCTGGACTGTGAAGAACACTGTGCAAAC
TCAGGATGACATCACAAGCATCCGGCTGTTGAAGCCGCAGGTTCTGCGGA
ATGTCTCGGGTGCTGAGAGCTGTTACCTTGCCCACAGCCTGCTGAAGTTC
TACTTGAACACTGTTTTCAAGAACTACCACAGCAAAATAGCCAAATTCAA
GGTCTTGAGGTCATTCTCCACTCTGGCCAACAACTTCATAGTCATCATGT
CACAACTACAGCCCAGTAAGGACAATTCCATGCTTCCCATTAGTGAGAGT
GCACACCAGCGGTTTTTGCTGTTCCGCAGAGCATTCAAACAGTTGGATAC
AGAAGTCGCTTTGGTGAAAGCCTTTGGGGAAGTGGACATTCTCCTGACCT
GGATGCAGAAATTCTACCATCTCTGATTCTAGAG (SEQ ID NO: 5, anexemplary full length coding sequence of murine IL-24 flanked by restriction enzyme sitesHind III and Xba I).

In some embodiments, the nucleic acid molecule includes a nucleic acid sequence encoding an amino acid sequence at least 95% identical to the amino acid sequence of SEQ ID NO: 1 or SEQ ID NO: 2, such as at least 95%, at least 96%, at least 97%, at least 98%, at least 99%, or 100% identical to the amino acid sequence of SEQ ID NO: 1 or SEQ ID NO: 2. In further embodiments, the nucleic acid molecule encodes a polypeptide that includes at most 1, 2, 3, 4, 5, 6, 7, 8, 9, or 10 conservative substitutions in SEQ ID NO: 1 or at most 1, 2, 3, 4, 5, 6, 7, 8, 9, or 10 conservative substitutions in SEQ ID NO: 2. In yet other embodiment, the nucleic acid molecule is at least 85% identical to SEQ ID NO: 3, SEQ ID NO: 4, or SEQ ID NO: 5, for example a nucleic acid molecule that is 85%, at least 90%, at least 95%, at least 96%, at least 97%, at least 98%, at least 99%, or 100% identical to SEQ ID NO: 3, SEQ ID NO: 4, or SEQ ID NO: 5.

These polynucleotides include DNA, cDNA, and RNA sequences that encode the IL-24 polypeptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3.sup.rd Edition, W.H. 5 Freeman and Co., NY).

Nucleic acid molecules encoding an IL-24 polypeptide, a variant thereof, or a fusion protein thereof can readily be produced by one of skill in the art using the amino acid sequences provided herein and the genetic code. Nucleic acid sequences encoding IL-24 can be prepared by any suitable method including, for example, cloning of appropriate sequences or by direct chemical synthesis by methods such as the phosphodiester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984 and the solid support method of U.S. Pat. No. 4,458,066. Chemical synthesis produces a single-strand (ss) oligonucleotide, which can be converted into double-strand (ds) DNA by hybridization with a complementary sequence or by polymerization with a DNA polymerase using the single strand as a template. Exemplary nucleic acids that include sequences encoding an IL-24 polypeptide can be prepared by cloning techniques.

A nucleic acid encoding an IL-24 polypeptide can be cloned or amplified by in vitro methods, such as the polymerase chain reaction (PCR), the ligase chain reaction (LCR), the transcription-based amplification system (TAS), the self-sustained sequence replication system (3SR), and the Qβ replicase amplification system (QB). For example, a polynucleotide encoding the protein can be isolated by a polymerase chain reaction of cDNA using primers based on the DNA sequence of the molecule. A wide variety of cloning and in vitro amplification methodologies are well-known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, N Y, 1989). Polynucleotides also can be isolated by screening genomic or cDNA libraries with probes selected from the sequences of the desired polynucleotide under stringent hybridization conditions.

In the context of the compositions and methods described herein, a nucleic acid sequence that encodes an IL-24 polypeptide, such as described above, a variant thereof, or a fusion protein thereof, is incorporated into a vector capable of expression in a host cell, using established molecular biology procedures. For example, nucleic acids, such as cDNAs, that encode an IL-24 polypeptide, a variant thereof, or a fusion protein thereof can be manipulated with standard procedures, such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate, or use of specific oligonucleotides in combination with PCR or other in vitro amplification.

Exemplary procedures sufficient to guide one of ordinary skill in the art through the production of a vector capable of expression in a host cell that includes a polynucleotide sequence encoding an IL-24 polypeptide, variant thereof, or fusion protein thereof can be found, for example, in Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2003); and Ausubel et al., *Short Protocols in Molecular Biology: A Compendium of Methods from Current Protocols in Molecular Biology*, 4th ed., Wiley & Sons, 1999.

Typically, a polynucleotide sequence encoding an IL-24 polypeptide, a variant thereof, or a fusion protein thereof, is operably linked to transcriptional control sequences including, for example a promoter and a polyadenylation signal. A promoter is a polynucleotide sequence recognized by the transcriptional machinery of the host cell (or introduced synthetic machinery) that is involved in the initiation of transcription. A polyadenylation signal is a polynucleotide sequence that directs the addition of a series of nucleotides on the end of the mRNA transcript for proper processing and trafficking of the transcript out of the nucleus into the cytoplasm for translation.

Exemplary promoters include viral promoters, such as cytomegalovirus immediate early gene promoter ("CMV"), herpes simplex virus thymidine kinase ("tk"), SV40 early transcription unit, polyoma, retroviruses, papilloma virus, hepatitis B virus, and human and simian immunodeficiency viruses. Other promoters are include promoters isolated from mammalian genes, such as the immunoglobulin heavy chain, immunoglobulin light chain, T cell receptor, HLA DQ α and DQ β, β-interferon, interleukin-2, interleukin-2 receptor, MHC class II, HLA-DRα, β-actin, muscle creatine kinase, prealbumin (transthyretin), elastase I, metallothionein, collagenase, albumin, fetoprotein, β-globin, c-fos, c-HA-ras, insulin, neural cell adhesion molecule (NCAM), al-antitrypsin, H2B (TH2B) histone, type I collagen, glucose-regulated proteins (GRP94 and GRP78), rat growth hormone, human serum amyloid A (SAA), troponin I (TNI), platelet-derived growth factor, and dystrophin, as well as promoters specific for T cells, including Th17 cells; keratinocytes; corneocytes; and epithelial cells.

The promoter can be either inducible or constitutive. An inducible promoter is a promoter that is inactive or exhibits low activity except in the presence of an inducer substance. Examples of inducible promoters include, but are not limited to, MT II, MMTV, collagenase, stromelysin, SV40, murine MX gene, α-2-macroglobulin, MHC class I gene h-2kb, HSP70, proliferin, tumor necrosis factor, or thyroid stimulating hormone gene promoter. Typically, the promoter is a constitutive promoter that results in high levels of transcription upon introduction into a host cell in the absence of additional factors. Optionally, transcription control sequences include one or more enhancer elements, which are binding recognition sites for one or more transcription factors that increase transcription above that observed for the minimal promoter alone.

It may be desirable to include a polyadenylation signal to effect proper termination and polyadenylation of the gene transcript. Exemplary polyadenylation signals have been isolated from bovine growth hormone, SV40, and the herpes simplex virus thymidine kinase genes.

The polynucleotides encoding an IL-24 polypeptide, a variant thereof, or a fusion protein thereof include a recombinant DNA which is incorporated into a vector in an autonomously replicating plasmid or virus or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single and double forms of DNA.

Viral vectors that encode the IL-24 polypeptide, a variant thereof, or a fusion protein thereof can also be prepared. A number of viral vectors have been constructed, including polyoma; SV40 (Madzak et al., 1992, J. Gen. Virol., 73:15331536); adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256); vaccinia virus (Mackett et al., 1992, Biotechnology, 24:495-499); adeno-associated virus (Muzyczka, 1992, Curr. Top. Microbiol. Immunol., 158:91-123; On et al., 1990, Gene, 89:279-282); herpes viruses, including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199); Sindbis viruses (H. Herweijer et al., 1995, Human Gene Therapy 6:1161-1167; U.S. Pat. Nos. 5,091,309 and 5,217,879); alphaviruses (S. Schlesinger, 1993, Trends Biotechnol. 11:18-22; I. Frolov et al., 1996, Proc. Natl. Acad. Sci. USA 93:11371-11377); and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (Autographa californica multinuclear polyhedrosis virus; AcMNPV) vectors are also known in the art and may be obtained from commercial sources (such as PharMingen, San Diego, Calif.; Protein Sciences Corp., Meriden, Conn.; Stratagene, La Jolla, Calif.).

Thus, in one embodiment, the polynucleotide encoding an IL-24 polypeptide, a variant thereof, or a fusion protein thereof is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors, and poliovirus vectors. Specific exemplary vectors are poxvirus vectors, such as vaccinia virus, fowlpox virus and a highly attenuated vaccinia virus (MVA), adenovirus, baculovirus, yeast, and the like.

It is understood that portions of the nucleic acid sequences encoding an IL-24 polypeptide can be deleted as long as the polypeptides are functionally active. For example, it may be desirable to delete one or more amino acids from the N-terminus, C-terminus, or both. It is also contemplated that substitution of residues in an IL-24 polypeptide can be, for example, conservative substitutions, such that the functionality of the IL-24 polypeptide is maintained (see above).

AAV Vectors

Disclosed herein are methods and compositions that can utilize one or more vectors, such as a viral vector, such as a retroviral vector or an adenoviral vector, or an AAV vector. Defective viruses, that entirely or almost entirely lack viral genes, can be used. Use of defective viral vectors allows for administration to specific cells without concern that the vector can infect other cells. The adenovirus and AAV vectors of use include replication-competent, replication-deficient, and helper-dependent ("gutless") forms thereof. Without being bound by theory, adenovirus vectors are known to exhibit strong expression in vitro, excellent titer, and the ability to transduce dividing and non-dividing cells in vivo (Hitt et al., Adv in Virus Res 55:479-505, 2000). When used in vivo, these vectors lead to strong, but transient, gene expression due to immune responses elicited to the vector backbone. In some non-limiting examples, a vector of use is an attenuated adenovirus vector, such as the vector described by Stratford-Perricaudet et al. (*J. Clin. Invest.*, 90:626-630 1992; La Salle et al., *Science* 259:988-990, 1993) or a defective AAV vector (Samulski et al., *J. Virol.*, 61:3096-3101, 1987; Samulski et al., *J. Virol.*, 63:3822-3828, 1989; Lebkowski et al., *Mol. Cell. Biol.*, 8:3988-3996, 1988).

Recombinant AAV vectors are characterized in that they are capable of directing the expression and the production of the selected transgenic products in targeted cells. Thus, the recombinant vectors comprise at least all of the sequences of AAV essential for encapsidation and the physical structures for infection of target cells.

AAV belongs to the family Parvoviridae and the genus *Dependovirus*. AAV is a small, non-enveloped virus that packages a linear, single-stranded DNA genome. Both sense and antisense strands of AAV DNA are packaged into AAV capsids with equal frequency. In some embodiments, the AAV DNA includes a nucleic acid encoding Pdx1 and MafA, but does not include a nucleic acid encoding Ngn3. Further provided are recombinant vectors, such as recombinant adenovirus vectors and recombinant adeno-associated virus (rAAV) vectors comprising a nucleic acid molecule disclosed herein. In some embodiments, the AAV is rAAV8 and/or AAV2. However, the AAV serotype can be any other suitable AAV serotype, such as AAV1, AAV2, AAV3, AAV4, AAV5, AAV6, AAV7, AAV9, AAV10, AAV11 or AAV12, or a hybrid of two or more AAV serotypes (such as, but not limited to AAV2/1, AAV2/7, AAV2/8 or AAV2/9).

The AAV genome is characterized by two inverted terminal repeats (ITRs) that flank two open reading frames (ORFs). In the AAV2 genome, for example, the first 125 nucleotides of the ITR are a palindrome, which folds upon itself to maximize base pairing and forms a T-shaped hairpin structure. The other 20 bases of the ITR, called the D sequence, remain unpaired. The ITRs are cis-acting sequences important for AAV DNA replication; the ITR is the origin of replication and serves as a primer for second-strand synthesis by DNA polymerase. The double-stranded DNA formed during this synthesis, which is called replicating-form monomer, is used for a second round of self-priming replication and forms a replicating-form dimer. These double-stranded intermediates are processed via a strand displacement mechanism, resulting in single-stranded DNA used for packaging and double-stranded DNA used for transcription. Located within the ITR are the Rep binding elements and a terminal resolution site (TRS). These features are used by the viral regulatory protein Rep during AAV replication to process the double-stranded intermediates. In addition to their role in AAV replication, the ITR is also essential for AAV genome packaging, transcription, negative regulation under non-permissive conditions, and site-specific integration (Daya and Berns, *Clin Microbiol Rev* 21(4):583-593, 2008). In some embodiments, these elements are included in the AAV vector.

The left ORF of AAV contains the Rep gene, which encodes four proteins—Rep78, Rep 68, Rep52 and Rep40. The right ORF contains the Cap gene, which produces three viral capsid proteins (VP1, VP2 and VP3). The AAV capsid contains 60 viral capsid proteins arranged into an icosahedral symmetry. VP1, VP2 and VP3 are present in a 1:1:10 molar ratio (Daya and Berns, *Clin Microbiol Rev* 21(4):583-593, 2008). In some embodiments, these elements are included in the AAV vector.

AAV vectors can be used for gene therapy. Exemplary AAV of use are AAV2, AAV5, AAV6, AAV8 and AAV9. Adenovirus, AAV2 and AAV8 are capable of transducing cells in the retina. Thus, any of a rAAV2 or rAAV8 vector can be used in the methods disclosed herein. However, rAAV6 and rAAV9 vectors are also of use.

Although AAV infects humans and some other primate species, it is not known to cause disease and elicits a very mild immune response. Gene therapy vectors that utilize AAV can infect both dividing and quiescent cells and persist in an extrachromosomal state without integrating into the genome of the host cell. AAV8 preferentially infects cells of the retina. Because of the advantageous features of AAV, the present disclosure contemplates the use of an rAAV for the methods disclosed herein.

AAV possesses several additional desirable features for a gene therapy vector, including the ability to bind and enter target cells, enter the nucleus, the ability to be expressed in the nucleus for a prolonged period of time, and low toxicity. AAV can be used to transfect cells, and suitable vector are known in the art, see for example, U.S. Published Patent Application No. 2014/0037585, incorporated herein by reference. Methods for producing rAAV suitable for gene therapy are well-known in the art (see, for example, U.S. Published Patent Application Nos. 2012/0100606; 2012/0135515; 2011/0229971; and 2013/0072548; and Ghosh et al., *Gene Ther* 13(4):321-329, 2006, all of which are incorporated herein by reference) and can be utilized with the methods disclosed herein.

In some embodiments, the vector is a rAAV8 vector, a rAAV6 vector, or a rAAV9 vector. In a specific non-limiting example, the vector is an AAV8 vector. AAV8 vectors are disclosed, for example, in U.S. Pat. No. 8,692,332, which is incorporated by reference herein. An exemplary AAV8 nucleic acid sequence is shown in FIG. 1 and SEQ ID NO:

1 of U.S. Pat. No. 8,692,332. It is disclosed that the AAV nucleic acid sequence can be greater than about 90%, 95%, 98% or 99% identical to this nucleic acid sequence. The location and sequence of the capsid, rep 68/78, rep 40/52, VP1, VP2, and VP3 are disclosed in this U.S. Pat. No. 8,692,332. The location and hypervariable regions of AAV8 are also provided.

The vectors of use in the methods disclosed herein can contain nucleic acid sequences encoding an intact AAV capsid which may be from a single AAV serotype (e.g., AAV2, AAV, 6, AAV8 or AAV9). As disclosed in U.S. Pat. No. 8,692,332, vectors of use can also can be recombinant, and thus can contain sequences encoding artificial capsids which contain one or more fragments of the AAV8 capsid fused to heterologous AAV or non-AAV capsid proteins (or fragments thereof). These artificial capsid proteins are selected from non-contiguous portions of the AAV2, AAV6, AAV8 or AAV9 capsid or from capsids of other AAV serotypes. For example, a rAAV vector may have a capsid protein comprising one or more of the AAV8 capsid regions selected from the VP2 and/or VP3, or from VP1, or fragments thereof selected from amino acids 1 to 184, amino acids 199 to 259; amino acids 274 to 446; amino acids 603 to 659; amino acids 670 to 706; amino acids 724 to 738 of the AAV8 capsid, see SEQ ID NO: 2 of U.S. Pat. No. 8,692,332. In another example, it may be desirable to alter the start codon of the VP3 protein to GTG. Alternatively, the rAAV may contain one or more of the AAV serotype 8 capsid protein hypervariable regions, for example, aa 185-198; aa 260-273; aa447-477; aa495-602; aa660-669; and aa707-723 of the AAV8 capsid set forth in SEQ ID NO: 2 of U.S. Pat. No. 8,692,332.

In some embodiments, a recombinant adeno-associated virus (rAAV) is generated having an AAV serotype 8 capsid. To produce the vector, a host cell that can be cultured that contains a nucleic acid sequence encoding an AAV serotype 8 capsid protein or fragment thereof, as defined herein; a functional rep gene; a minigene composed of, at a minimum, AAV inverted terminal repeats (ITRs) and a transgene, such as a transgene encoding IL-24 or a functional fragment thereof, such as including the amino acid sequence of SEQ ID NO: 1 or SEQ ID NO: 2; and sufficient helper functions to permit packaging in the AAV8 capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell that has been engineered to contain one or more of the required components using methods known to those of skill in the art. In some embodiments, a stable host cell will contain the required component(s) under the control of an inducible promoter or a tissue specific promoter. Similar methods can be used to generate a rAAV2, rAAV6, or rAAV9 vector and/or virion.

The tissue specific promoter can be a retinal specific promoter, such as photoreceptor specific promoter, for example, a rhodopsin kinase (RK) promoter. The rhodopsin kinase promoter directs expression in rod and cone cells. This promoter has been optimized for expression (see Khani et al., Invest. Opthamol. Vis. Science, 48: 3954-3961, 2007, incorporated herein by reference). The sequence of this promoter is provided in FIG. 1 of this reference. Additional promoters include, but are not limited to, NRL, CRX, IRBP, or rhodopsin promoters. In other embodiments, component(s), such as, but not limited to, a transgene encoding IL-24, a variant, fusion protein, or a functional fragment thereof, such as the amino acid sequence of SEQ ID NO: 1 or SEQ ID NO: 2, can be under the control of a constitutive promoter. A non-limiting example of a suitable constitutive promoter is the cytomegalovirus promoter. Additional non-limiting examples are the ubiquitin (such as U6) or an H1 promoter. Promoters of use are also disclosed in the section above.

In still another alternative, a selected stable host cell may contain selected component(s) under the control of a constitutive promoter and other selected component(s) under the control of one or more inducible promoters. For example, a stable host cell may be generated that is derived from 293 cells (which contain E1 helper functions under the control of a constitutive promoter) but that contains the rep and/or cap proteins under the control of inducible promoters. Still other stable host cells may be generated by one of skill in the art.

The minigene, rep sequences, cap sequences, and helper functions required for producing a rAAV can be delivered to the packaging host cell in the form of any genetic element that transfers the sequences carried thereon. The selected genetic element may be delivered by any suitable method, including those described herein. The methods used to construct vectors are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well-known, and the selection of a suitable method is not a limitation on the present invention. See, e.g., K. Fisher et al, J. Virol., 70:520-532 (1993) and U.S. Pat. No. 5,478,745. In some embodiments, selected AAV components can be readily isolated using techniques available to those of skill in the art from an AAV serotype, including AAV8. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases (e.g., GENBANK®).

Pharmaceutical Compositions and the Treatment of Ocular Surface Inflammation and Uveitis Provided herein are pharmaceutical compositions that include the IL-24 polypeptides, variants, and fusion proteins or a polynucleotides encoding the IL-24 polypeptides, variants, and fusion proteins disclosed herein. The pharmaceutical compositions can be formulated and administered in a variety of ways depending on the location and type of disease to be treated (see, e.g., U.S. Published Application No. 20050054567, which discloses pharmaceutical compositions of IL-24 polypeptides and variants thereof as well as administration of such compositions and is incorporated herein by reference). These pharmaceutical compositions are of use in the methods disclosed herein.

Pharmaceutical compositions are provided for both local use (for example, topical or on an ocular surface) and systemic use. As the subject can be any subject, such as a mammalian or human subject. The disclosure includes within its scope pharmaceutical compositions comprising IL-24 polypeptide, variant thereof, or fusion protein thereof that suppresses production of effector cytokines by Th17 cells. The disclosure also includes within its scope a pharmaceutical composition including a nucleic acid molecule encoding the IL-24 polypeptide, variant thereof, or fusion protein thereof. The pharmaceutical compositions can be formulated for use in human or veterinary medicine.

The IL-24 polypeptides, variants thereof, or fusion proteins thereof and nucleic acid molecules encoding IL-24 polypeptides, variants thereof, or fusion proteins thereof can be administered ex vivo (such as into a stem cell to be implanted into the eye) or in vivo to a cell or subject. Generally, it is desirable to prepare the compositions as pharmaceutical compositions appropriate for the intended application. Accordingly, methods for making a medicament or pharmaceutical composition containing the polypeptides, nucleic acid molecules, or vectors described above are included herein. Typically, preparation of a pharmaceutical composition (medicament) entails preparing a pharmaceutical composition that is essentially free of pyrogens as well as any other impurities that could be harmful to humans or animals. Typically, the pharmaceutical composition contains appropriate salts and buffers to render the components of the composition stable. In some examples, the release rate of IL-24 can be modulated (e.g., decreased) by co-administering an antibody specific for a pharmaceutical composition that includes L-24 polypeptides, variants, and fusion proteins (see, e.g., Webster et al., J Exp Med., 206(4): 751-760, 2009; Courtney et al., Immunopharmacology, 28(3):223-32, 1994, incorporated by reference herein). Monoclonal antibodies that specifically bind IL-24 re commercial available form R&D Systems, Abcam, Novus, and Thermo Fisher Scientific, among others.

In some embodiments, polynucleotides are utilized, such as in viral vectors, such as AAV vectors. For example, the virus can be delivered by microinjection, electroporation, lipid-mediated transfection, peptide-mediated delivery, or other methods known in the art. For in vivo delivery, a vector, such as an adenovirus or an AAV vector, can be formulated into a pharmaceutical composition and will generally be administered locally to the eye, such as intravitreally or subretinally. Appropriate doses of a viral vector depend on the subject being treated (e.g., human or nonhuman primate or other mammal), age and general condition of the subject to be treated, the severity of the condition being treated, and the mode of administration of the vector/virion, among other factors. An appropriate effective amount can be readily determined by one of skill in the art. Thus, a "therapeutically effective amount" will fall in a relatively broad range that can be determined through clinical trials.

The viral vector, such as, but not limited to, an AAV vector, may be formulated to permit release over a specific period of time. A release system can include a matrix of a biodegradable material or a material which releases the incorporated components by diffusion. The components can be homogeneously or heterogeneously distributed within the release system.

A variety of release systems may be useful; however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because, generally, they are more reliable, more reproducible and produce more defined release profiles. The release system material can be selected so that components having different molecular weights are released by diffusion through or degradation of the material.

Representative synthetic, biodegradable polymers include, for example, polyamides, such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions and/or additions of chemical groups, for example, alkyl and/or alkylene groups; hydroxylations; oxidations; and other modifications routinely made by those skilled in the art), copolymers, and mixtures thereof. Representative synthetic, non-degradable polymers include, for example, polyethers, such as poly(ethylene oxide), poly(ethylene glycol), and poly(tetramethylene oxide); vinyl polymers-polyacrylates and polymethacrylates, such as methyl, ethyl, other alkyls, hydroxyethyl methacrylate, acrylic and methacrylic acids, and others, such as poly(vinyl alcohol), poly(vinyl pyrolidone), and poly(vinyl acetate); poly(urethanes); cellulose and its derivatives, such as alkyl, hydroxyalkyl, ethers, esters, nitrocellulose, and various cellulose acetates; polysiloxanes; and any chemical derivatives thereof (substitutions and/or additions of chemical groups, for example, alkyl and/or alkylene groups; hydroxylations; oxidations; and other modifications routinely made by those skilled in the art), copolymers and mixtures thereof.

Poly(lactide-co-glycolide) microspheres can also be used for intraocular injection. Typically, the microspheres are composed of a polymer of lactic acid and glycolic acid, which are structured to form hollow spheres. The spheres can be approximately 15-30 microns in diameter and can be loaded with components described herein.

For example, for in vivo injection (i.e., injection directly to the subject), a therapeutically effective dose will be on the order of from about $10^5$ to $10^{16}$ of the AAV virions, such as $10^8$ to $10^{14}$ AAV virions. The dose, of course, depends on the efficiency of transduction, promoter strength, the stability of the message and protein encoded thereby, and clinical factors. Effective dosages can be readily established by one of ordinary skill in the art through routine trials that establish dose-response curves.

In some embodiments, if the subject composition is an AAV, an effective amount to achieve a change will be about $1 \times 10^8$ vector genomes or more, in some cases about $1 \times 10^9$, about $1 \times 10^{10}$, about $1 \times 10^{11}$, about $1 \times 10^{12}$, or about $1 \times 10^{13}$ vector genomes or more, in certain instances, about $1 \times 10^{14}$ vector genomes or more, and usually no more than about $1 \times 10^{15}$ vector genomes. In some embodiments, the amount of vector that is delivered is about $1 \times 10^{14}$ vectors or less, for example, about $1 \times 10^{13}$, about $1 \times 10^{12}$, about $1 \times 10^{11}$, about $1 \times 10^{10}$, or about $1 \times 10^9$ vectors or less, in certain instances about $1 \times 10^8$ vectors, and typically no less than $1 \times 10^8$ vectors. In some non-limiting examples, the amount of vector genomes delivered is about $1 \times 10^{10}$ to about $1 \times 10^{11}$ vectors. In additional non-limiting examples, the amount of vector delivered is about $1 \times 10^{10}$ to about $1 \times 10^{12}$ vector genomes.

In some embodiments, the amount of pharmaceutical composition to be administered may be measured using multiplicity of infection (MOI). In some embodiments, MOI refers to the ratio or multiple of vector or viral genomes to the cells to which the nucleic may be delivered. In some embodiments, the MOI may be about $1 \times 10^6$. In some cases, the MOI can be about $1 \times 10^5$ to about $1 \times 10^7$. In some cases, the MOI may be about $1 \times 10^4$ to about $1 \times 10^8$. In some cases, recombinant viruses of the disclosure are at least about $1 \times 10^1$, about $1 \times 10^2$, about $1 \times 10^3$, about $1 \times 10^4$, about $1 \times 10^5$, about $1 \times 10^6$, about $1 \times 10^7$, about $1 \times 10^8$, about $1 \times 10^9$, about $1 \times 10^{10}$, about $1 \times 10^{11}$, about $1 \times 10^{12}$, about $1 \times 10^{13}$, about $1 \times 10^{14}$, about $1 \times 10^{15}$, about $1 \times 10^{16}$, about $1 \times 10^{17}$, or about $1 \times 10^{18}$ MOI. In some cases, recombinant viruses of this disclosure are about $1 \times 10^8$ to $1 \times 10^{14}$ MOI.

In some examples, the amount of pharmaceutical composition delivered comprises about $1 \times 10^8$ to about $1 \times 10^{15}$ particles of recombinant viruses, about $1 \times 10^9$ to about $1 \times 10^{14}$ particles of recombinant viruses, about $1 \times 10^{10}$ to about $1 \times 10^{13}$ particles of recombinant viruses, or about $1 \times 10^{11}$ to about $1 \times 10^{12}$ particles of recombinant viruses (see U.S. Published Patent Application No. 2015/0259395, incorporated herein by reference).

Dosage treatment may be a single dose schedule or a multiple dose schedule to ultimately deliver the amount specified above. Moreover, the subject may be administered as many doses as appropriate. Thus, the subject may be given, for example, $10^5$ to $10^{16}$ AAV virions in a single dose, or two, four, five, six or more doses that collectively result in delivery of, for example, $10^5$ to $10^{16}$ AAV virions. One of skill in the art can readily determine an appropriate number of doses to administer.

In some embodiments, the AAV is administered at a dose of about $1 \times 10^{11}$ to about $1 \times 10^{14}$ viral particles (vp)/kg. In some examples, the AAV is administered at a dose of about $1 \times 10^{12}$ to about $8 \times 10^{13}$ vp/kg. In other examples, the AAV is administered at a dose of about $1 \times 10^{13}$ to about $6 \times 10^{13}$ vp/kg. In specific, non-limiting examples, the AAV is administered at a dose of at least about $1 \times 10^{11}$, at least about $5 \times 10^{11}$, at least about $1 \times 10^{12}$, at least about $5 \times 10^{12}$, at least about $1 \times 10^{13}$, at least about $5 \times 10^{13}$, or at least about $1 \times 10^{14}$ vp/kg. In other non-limiting examples, the rAAV is administered at a dose of no more than about $5 \times 10^{11}$, no more than about $1 \times 10^{12}$, no more than about $5 \times 10^{12}$, no more than about $1 \times 10'$, no more than about $5 \times 10^{13}$, or no more than about $1 \times 10^{14}$ vp/kg. In one non-limiting example, the AAV is administered at a dose of about $1 \times 10^{12}$ vp/kg. The AAV can be administered in a single dose or in multiple doses (such as 2, 3, 4, 5, 6, 7, 8, 9, or 10 doses) as needed for the desired therapeutic results.

The pharmaceutical compositions can contain the vector, such as the AAV vector, and/or virions and a pharmaceutically acceptable excipient. Such excipients include any pharmaceutical agent that does not itself induce the production of antibodies harmful to the individual receiving the composition and that may be administered without undue toxicity. Pharmaceutically acceptable excipients include, but are not limited to, liquids such as water, saline, glycerol, and ethanol. Pharmaceutically acceptable salts can be included therein, for example, mineral acid salts, such as hydrochlorides, hydrobromides, phosphates, sulfates, and the like, and salts of organic acids, such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., N.J. 1991).

In some embodiments, the excipients confer a protective effect on the AAV virion such that loss of AAV virions as well as transduceability resulting from formulation procedures, packaging, storage, transport, and the like is minimized. Therefore, these excipient compositions are considered "virion-stabilizing" because they provide higher AAV virion titers and higher transduceability levels than their non-protected counterparts, as measured using standard assays (see, for example, Published U.S. Application No. 2012/0219528, incorporated herein by reference). Therefore, these compositions demonstrate "enhanced transduceability levels" compared with compositions lacking the particular excipients described herein and are, thus, more stable than their non-protected counterparts.

Exemplary excipients that can used to protect the AAV virion from activity degradative conditions include, but are not limited to, detergents, proteins (e.g., ovalbumin and bovine serum albumin), amino acids (e.g., glycine), polyhydric and dihydric alcohols (e.g., polyethylene glycols (PEG) of varying molecular weights, such as PEG-200, PEG-400, PEG-600, PEG-1000, PEG-1450, PEG-3350, PEG-6000, PEG-8000 and any molecular weights in between these values, with molecular weights of 1500 to 6000 preferred), propylene glycols (PG), and sugar alcohols (such as a carbohydrate, preferably, sorbitol). The detergent, when present, can be an anionic, a cationic, a zwitterionic, or a nonionic detergent. An exemplary detergent is a nonionic detergent. One suitable type of nonionic detergent is a sorbitan ester (e.g., polyoxyethylenesorbitan monolaurate (TWEEN®-20) polyoxyethylenesorbitan monopalmitate (TWEEN®-40), polyoxyethylenesorbitan monostearate (TWEEN®-60), polyoxyethylenesorbitan tristearate (TWEEN®-65), polyoxyethylenesorbitan monooleate (TWEEN®-80), polyoxyethylenesorbitan trioleate (TWEEN®-85), such as TWEEN®-20 and/or TWEEN®-80). These excipients are commercially available from a number of vendors, such as Sigma, St. Louis, Mo.

The amount of the various excipients present in any of the disclosed compositions, including AAV, varies and is readily determined by one of skill in the art. For example, a protein excipient, such as BSA, if present, can be present at a concentration of between 1.0 weight (wt.) % to about 20 wt. %, preferably 10 wt. %. If an amino acid, such as glycine, is used in the formulations, it can be present at a concentration of about 1 wt. % to about 5 wt. %. A carbohydrate, such as sorbitol, if present, can be present at a concentration of about 0.1 wt % to about 10 wt. %, such as between about 0.5 wt. % to about 15 wt. % or about 1 wt. % to about 5 wt. %. If polyethylene glycol is present, it can generally be present on the order of about 2 wt. % to about 40 wt. %, such as about 10 wt. % top about 25 wt. %. If propylene glycol is used in the subject formulations, it will typically be present at a concentration of about 2 wt. % to about 60 wt. %, such as about 5 wt. % to about 30 wt. %. If a detergent, such as a sorbitan ester (TWEEN®), is present, it can be present at a concentration of about 0.05 wt. % to about 5 wt. %, such as between about 0.1 wt. % and about 1 wt % (see U.S. Published Patent Application No. 2012/0219528, which is incorporated herein by reference). In one example, an aqueous virion-stabilizing formulation comprises a carbohydrate, such as sorbitol, at a concentration of between 0.1 wt. % to about 10 wt. %, such as between about 1 wt. % to about 5 wt. %, and a detergent, such as a sorbitan ester (TWEEN®) at a concentration of between about 0.05 wt. % and about 5 wt. %, such as between about 0.1 wt. % and about 1 wt. %. Virions are generally present in the composition in an amount sufficient to provide a therapeutic effect when given in one or more doses, as defined above.

Therapeutic compositions can be provided as parenteral compositions, such as for injection or infusion. Such compositions are formulated generally by mixing a disclosed therapeutic agent at the desired degree of purity in a unit dosage injectable form (solution, suspension, or emulsion) with a pharmaceutically acceptable carrier, for example, one that is non-toxic to recipients at the dosages and concentrations employed and is compatible with other ingredients of the formulation. In addition, a disclosed therapeutic agent can be suspended in an aqueous carrier, for example, in an isotonic or hypotonic buffer solution at a pH of about 3.0 to about 8.5, such as about 4.0 to about 8.0, about 6.5 to about 8.5, or about 7.4. Useful buffers include saline-buffered phosphate or an ionic boric acid buffer. The active ingredient, optionally together with excipients, can also be in the form of a lyophilisate and can be made into a solution prior to parenteral administration by the addition of suitable solvents. Solutions, such as those that are used for parenteral administration, can also be used as infusion solutions.

In some examples, the IL-24 polypeptide, variant thereof, or fusion protein thereof or nucleic acid molecule encoding the IL-24 polypeptide, variant thereof, or fusion protein thereof can be included in an excipient, such as an inert matrix for either topical application or injection into the eye, such as for intra-vitreal or subretinal administration. As one example of an inert matrix, liposomes may be prepared from dipalmitoyl phosphatidylcholine (DPPC), such as egg phosphatidylcholine (PC). Liposomes, including cationic and anionic liposomes, can be made using standard procedures as known to one skilled in the art. For some applications, liposomes that include an IL-24 polypeptide, variant thereof, fusion protein thereof or a nucleic acid molecule encoding the IL-24 polypeptide, variant thereof, or fusion protein thereof can be injected intraocularly. In a formulation for intraocular injection, the liposome capsule degrades due to cellular digestion. Without being bound by theory, these formulations provide the advantages of a slow-release drug delivery system, exposing a subject to a substantially constant concentration of the IL-24 polypeptide, variant thereof, or fusion protein thereof or nucleic acid molecule encoding the IL-24 polypeptide, variant thereof, or fusion protein thereof over time. In some examples, the IL-24 polypeptide, variant thereof, or fusion protein thereof or nucleic acid molecule encoding the IL-24 polypeptide, variant thereof, or fusion protein thereof can be dissolved in an organic solvent, such as DMSO or alcohol, as previously described, and contain a polyanhydride, poly(glycolic) acid, poly(lactic) acid, or polycaprolactone polymer.

Pharmaceutical compositions can include an effective amount of the polypeptide, nucleic acid molecule, or dispersed (for example, dissolved or suspended) in a pharmaceutically acceptable carrier or excipient. Pharmaceutically acceptable carriers and/or pharmaceutically acceptable excipients are known in the art and are described, for example, in *Remington's Pharmaceutical Sciences* by E. W. Martin, Mack Publishing Co., Easton, Pa., 19$^{th}$ Edition, 1995.

The nature of the carrier will depend on the particular mode of administration being employed. For example, parenteral formulations usually contain injectable fluids that include pharmaceutically and physiologically acceptable fluids, such as water, physiological saline, balanced salt solutions, aqueous dextrose, glycerol, or the like, as a vehicle. For solid compositions (such as powder, pill, tablet, or capsule forms), conventional non-toxic solid carriers can include, for example, pharmaceutical grades of mannitol, lactose, starch, or magnesium stearate. In addition, pharmaceutical compositions to be administered can contain minor amounts of non-toxic auxiliary substances, such as wetting or emulsifying agents, preservatives, pH buffering agents, and the like, for example, sodium acetate or sorbitan monolaurate.

As used herein, "pharmaceutically acceptable carrier" includes any and all solvents, dispersion media, coatings, antibacterial and antifungal agents, isotonic and absorption-delaying agents, and the like. The use of such media and agents for pharmaceutically active substances is well-known in the art. Except insofar as any conventional media or agent is incompatible with the active ingredient, its use in the pharmaceutical compositions is contemplated. Supplementary active ingredients can also be incorporated into the compositions. For example, certain pharmaceutical compositions can include the vectors or viruses in water, mixed with a suitable surfactant, such as hydroxypropylcellulose. Dispersions also can be prepared in glycerol, liquid polyethylene glycols, and mixtures thereof as well as in oils. Under ordinary conditions of storage and use, these preparations contain a preservative to prevent the growth of microorganisms.

Administration of therapeutic compositions can be by any common route as long as the target tissue (typically, the eye) is available via that route. This includes oral, nasal, ocular, buccal, or other mucosal (such as rectal or vaginal) or topical administration. Alternatively, administration will be by orthotopic, intradermal subcutaneous, intramuscular, intraperitoneal, or intravenous injection routes. In some embodiments, the IL-24 polypeptide, variant thereof, or fusion protein thereof or the polynucleotide encoding the IL-24 polypeptide, variant thereof, or fusion protein is formulated for administration to the eye, such as to the cornea, uveal tract, or conjunctiva. Such pharmaceutical compositions are usually administered as pharmaceutically acceptable compositions that include physiologically acceptable carriers, buffers, or other excipients. Pharmaceutical compositions that include an IL-24 polypeptide, variant thereof, or fusion protein thereof or a polynucleotide encoding the IL-24 polypeptide, variant thereof, or fusion protein thereof as an active ingredient can be formulated with an appropriate solid or liquid carrier, depending upon the particular mode of administration chosen.

The pharmaceutically acceptable carriers and excipients useful in this disclosure are conventional. For instance, parenteral formulations usually comprise fluids that are pharmaceutically and physiologically acceptable fluid vehicles, such as water, physiological saline, other balanced salt solutions, aqueous dextrose, glycerol, or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, pH-buffering agents, and the like, for example, sodium acetate or sorbitan monolaurate.

The dosage form of the pharmaceutical composition will be determined by the mode of administration chosen. For instance, in addition to injectable fluids, topical and oral formulations can be employed. Topical preparations can include eye drops, ointments, sprays, and the like. Eye drops or sprays can be provided in unit dose dispensers (such as eye drop bottles that dispense a metered unit dose containing the IL-24 polypeptide, variant thereof, or fusion protein or polynucleotide encoding the IL-24 polypeptide, variant thereof, or fusion protein, either alone or in combination with other therapeutic agents, such as corticosteroids). Oral formulations may be liquid (e.g., syrups, solutions, or suspensions) or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known or will be apparent to those of ordinary skill in the art. Implants can also be employed (see below).

The pharmaceutical compositions that include an IL-24 polypeptide, variant thereof, or fusion protein thereof or a nucleic acid molecule encoding the IL-24 polypeptide, variant thereof, or fusion protein thereof will, in some embodiments, be formulated in unit dosage form, suitable for individual administration of precise dosages. The amount of active compound(s) administered will depend on the subject being treated, the severity of the affliction, and the manner of administration and is best left to the judgment of the prescribing clinician. Within these bounds, the formulation to be administered will contain a quantity of the active component(s) in amounts effective to achieve the desired effect in the subject being treated.

The IL-24 polypeptide, variant thereof, or fusion protein thereof or nucleic acid molecule encoding the IL-24 polypeptide, variant thereof, or fusion protein thereof can be included in an inert matrix for either topical application or injection into the eye, such as for intra-vitreal administration. As one example of an inert matrix, liposomes may be prepared from dipalmitoyl phosphatidylcholine (DPPC), such as egg phosphatidylcholine (PC). Liposomes, including cationic and anionic liposomes, can be made using standard procedures as known to one skilled in the art. For some applications, liposomes that include an IL-24 polypeptide, variant thereof, fusion protein thereof or a nucleic acid molecule encoding the IL-24 polypeptide, variant thereof, or fusion protein thereof can be applied topically, either in the form of drops or as an aqueous based cream, or can be injected intraocularly. In a formulation for topical application, an IL-24 polypeptide, variant thereof, or fusion protein thereof or a nucleic acid molecule encoding the IL-24 polypeptide, variant thereof, or fusion protein thereof is slowly released over time as the liposome capsule degrades due to wear and tear from the eye surface. In a formulation for intraocular injection, the liposome capsule degrades due to cellular digestion. Both of these formulations provide the advantages of a slow-release drug delivery system, exposing a subject to a substantially constant concentration of the IL-24 polypeptide, variant thereof, or fusion protein thereof or nucleic acid molecule encoding the IL-24 polypeptide, variant thereof, or fusion protein thereof over time. In one example, the IL-24 polypeptide, variant thereof, or fusion protein thereof or nucleic acid molecule encoding the IL-24 polypeptide, variant thereof, or fusion protein thereof can be dissolved in an organic solvent, such as DMSO or alcohol, as previously described, and contain a polyanhydride, poly (glycolic) acid, poly(lactic) acid, or polycaprolactone polymer.

The IL-24 polypeptide, variant thereof, or fusion protein thereof or nucleic acid molecule encoding the IL-24 polypeptide, variant thereof, or fusion protein thereof can be included in a delivery system that can be implanted at various sites in the eye, depending on the size, shape, and formulation of the implant as well as the type of transplant procedure. The IL-24 polypeptide, variant thereof, or fusion protein thereof or nucleic acid molecule encoding the IL-24 polypeptide, variant thereof, or fusion protein thereof can be used alone. However, in another embodiment, at least one additional agent, such as at least one agent that is disclosed below, can be included along with the IL-24 polypeptide, variant thereof, or fusion protein thereof or nucleic acid molecule encoding the IL-24 polypeptide, variant thereof, or fusion protein thereof in the delivery system, such as in an implant. The delivery system is then introduced into the eye. Suitable sites include, but are not limited to, the anterior chamber, anterior segment, posterior chamber, posterior segment, vitreous cavity, suprachoroidal space, subconjunctiva, episcleral, intracorneal, epicorneal, and sclera.

The implants can be inserted into the eye by a variety of methods, including placement by forceps or by trocar following making an incision in the sclera (for example, a 2-3 mm incision) or other suitable site. In some cases, the implant can be placed by trocar without making a separate incision, but instead by forming a hole directly into the eye with the trocar. The method of placement can influence the release kinetics. For example, implanting the device into the vitreous or the posterior chamber with a trocar may result in placement of the device deeper within the vitreous than placement by forceps, which may result in the implant being closer to the edge of the vitreous. The location of the implanted device may influence the concentration gradients of the IL-24 polypeptide, variant thereof, or fusion protein thereof or nucleic acid molecule encoding the IL-24 polypeptide, variant thereof, or fusion protein thereof surrounding the device and, thus, influence the release rates (for example, a device placed closer to the edge of the vitreous may result in a slower release rate; see U.S. Pat. Nos. 5,869,079 and 6,699,493, incorporated herein by reference).

The use of implants in the eye is well-known in the art (see U.S. Pat. Nos. 6,699,493 and 5,869,079, incorporated herein by reference). In one embodiment, an implant is formulated with the IL-24 polypeptide, variant thereof, or fusion protein thereof or nucleic acid molecule encoding the IL-24 polypeptide, variant thereof, or fusion protein thereof that is associated with a bio-erodible polymer matrix.

Generally, when implants are used, the IL-24 polypeptide, variant thereof, or fusion protein thereof or nucleic acid molecule encoding the IL-24 polypeptide, variant thereof, or fusion protein thereof is homogeneously distributed through the polymeric matrix, such that it is distributed evenly enough that no detrimental fluctuations in rate of release occur due to uneven distribution in the polymer matrix. The selection of the polymeric composition to be employed varies with the desired release kinetics, the location of the implant, patient tolerance, and the nature of the implant procedure. The polymer can be included as at least about 10 weight percent of the implant. In one example, the polymer is included as at least about 20 weight percent of the implant. In another embodiment, the implant comprises more than one polymer. These factors are described in detail in U.S. Pat. No. 6,699,493 (incorporated herein by reference). Characteristics of the polymers generally include biodegradability at the site of implantation, compatibility with the agent of interest, ease of encapsulation, and water insolubility, amongst others. Generally, the polymeric matrix is not fully degraded until the drug load has been released. The chemical composition of suitable polymers is known in the art (for example, see U.S. Pat. No. 6,699,493). The IL-24 polypeptide, variant thereof, or fusion protein thereof or nucleic acid molecule encoding the IL-24 polypeptide, variant thereof, or fusion protein thereof disclosed herein can be formulated in an implantable form with other carriers and solvents. For example, buffering agents and preservatives can be employed. The implant sizes and shape can also be varied for use in particular regions of the eye (see U.S. Pat. No. 5,869,079, incorporated herein by reference).

The IL-24 polypeptide, variant thereof, or fusion protein thereof or nucleic acid molecule encoding the IL-24 polypeptide, variant thereof, or fusion protein thereof encoding these polypeptides can be included in a contact lens, such as a bandage lens, for treating corneal inflammation in a subject. The contact lens includes a contact lens substrate and a coating provided on at least a portion of the substrate or within the matrix of the lens material. The coating can include an amount of an IL-24 polypeptide, variant thereof, or fusion protein thereof or a nucleic acid molecule encoding the IL-24 polypeptide, variant thereof, or fusion protein thereof effective to treat corneal inflammation in a subject upon administration of the contact lens to the subject.

Coatings that include the IL-24 polypeptide, variant thereof, or fusion protein thereof or nucleic acid molecule encoding the IL-24 polypeptide, variant thereof, or fusion protein thereof can be applied to a number of contact lens substrate materials known in the art. Virtually any substrate known in the art that can be fashioned into a contact lens can be used provided it is optically transparent.

In some embodiments, the substrate can include optically transparent materials that allow oxygen to reach the cornea in an amount, which is sufficient for long-term corneal health. Examples of substrates include polymers made from hydrophobic materials, such as silicone copolymers, interpolymers, oligomers, and macromers. Illustrative polysilicones are polydimethyl siloxane, and polydimethyl-co-vinylmethylsiloxane. Other silicones include silicone rubbers described in U.S. Pat. Nos. 3,228,741; 3,341,490; and 3,518,324. Substrates described in U.S. Pat. Nos. 4,136,250; 5,387,623; 5,760,100; 5,789,461; 5,776,999; 5,849,811; 5,314,960; and 5,244,981 can also be used. Cross-linked polymers of propoxylate of methyl glucose and propylene oxide and HEMA-based hydrogels can also be used as substrates of the contact lens.

Silicone compositions that can be used in forming the contact lens are the cross-linked polysiloxanes obtained by cross-linking siloxane prepolymers by means of hydrosilylation and co-condensation as well as by free radical mechanisms, as in U.S. Pat. No. 4,143,949. Additional silicone-based substrates are cross-linked polymers of α, ω-bis (aminopropyl)polydimethylsiloxane and glycidyl methacrylate-cross-linked polymers. Silicone compositions can also be made from combining a methacrylate with one or more silicone monomers in the presence of a group transfer polymerization (GTP) catalyst to form a macromer that is subsequently polymerized with other monomers to give the final substrate. Substrates described in U.S. Pat. No. 6,951,894 are also suitable for use in the present invention.

The IL-24 polypeptide, variant thereof, or fusion protein thereof or nucleic acid molecule encoding the IL-24 polypeptide, variant thereof, or fusion protein thereof can be prepared and applied to the contact lens as an aqueous solution, suspension, or colloid and then applied to the contact lens substrate according to any process that can provide the coating in contact with the substrate or cause the IL-24 polypeptide, variant thereof, or fusion protein thereof or nucleic acid molecule encoding the IL-24 polypeptide, variant thereof, or fusion protein thereof to be absorbed within the contact lens. For example, processes for applying the coating to the substrate include immersion, spraying, brushing, and spin coating. Once the lens substrate is coated, it may be subjected to any number of additional steps that are conducted in the manufacture of contact lenses. These can include, for example, swelling and washing steps; the addition of additives, such as surfactants; and extraction steps, among others. The solution that includes an IL-24 polypeptide, variant thereof, or fusion protein thereof or a nucleic acid molecule encoding the IL-24 polypeptide, variant thereof, or fusion protein thereof as disclosed herein can adhere to the contact lens by, for example, chemical bonding, such as covalent or ionic bonding or physical bonding. In some aspects, the coating is released from the lens substrate throughout its useful life (such as storage time plus the time in which it will be in contact with a user's eye).

The contact lens can also include more than one layer of coating. This can be desirable where the coating layer will provide the requisite surface properties (e.g., treatment of corneal inflammation) but is not particularly compatible with the lens substrate itself. For example, a tie-layer or coupling agent can be used to adhere the coating to the substrate. Selections of compatible lens substrate, therapeutic coating, and tie-layer (if necessary) materials is well within the knowledge of one skilled in the art. Generally, the contact lens is non-toxic to the subject's cornea and other tissue, while providing for the treatment of corneal inflammation in the subject.

An IL-24 polypeptide, variant thereof, or fusion protein thereof or a nucleic acid molecule encoding the IL-24 polypeptide, variant thereof, or fusion protein thereof described herein can be formulated with other carriers and solvents. For example, buffering agents and preservatives can be employed. Water soluble preservatives include sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol, and phenylethyl alcohol. These agents can be present in individual amounts of from about 0.001 to about 5% by weight, such as about 0.01 to about 2%. Suitable water soluble buffering agents that may be employed are sodium carbonate, sodium borate, sodium phosphate, sodium acetate, and sodium bicarbonate. These agents can be present in amounts sufficient to maintain a pH of the system of between about 2 to about 9, such as about 4 to about 8, or about 6 to about 7. In some examples, the pH of the system is maintained at about 7, about 7.2, about 7.4, about 7.6, or about 7.8. As such, the buffering agent can be as much as 5% on a weight-to-weight basis of the total composition. Electrolytes, such as sodium chloride and potassium chloride, may also be included in the formulation. The proportions of the IL-24 polypeptide, variant thereof, or fusion protein thereof or nucleic acid molecule encoding the IL-24 polypeptide, variant thereof, or fusion protein thereof; added polymers; and any other modifiers may be empirically determined by formulating several implants with varying proportions. A USP-approved method for dissolution or release test can be used to measure the rate of release (USP 23; NF 18, pp. 1790-1798, 1995).

The IL-24 polypeptide, variant thereof, or fusion protein thereof or nucleic acid molecule encoding the IL-24 polypeptide, variant thereof, or fusion protein thereof can be formulated with additional therapeutic agents. Exemplary agents include anti-inflammatory agents, immunosuppressive agents, antibacterial agents, antifungal agents, or immunomodulatory agents. In some examples, the additional therapeutic agent is a corticosteroid, such as a glucocorticoid or calcineurin antagonist. Exemplary glucocorticoids include dexamethasone, fluocinolone, difluprednate, triamcinolone, rimexolone, loteprednol, prednisolone, and fluorometholone. Exemplary calcineurin antagonists include ciclosporin, sirolimus, and tacrolimus.

Exemplary antibiotics include idoxuridine, gatifloxacin, sulfacetamide, levofloxacin, tobramycin, polymyxin, trifluridine, ganciclovir, povidone iodine, chloramphenicol, minoglycosides (for example, amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, and trospectomycin), amphenicols (for example, azidamfenicol, chloramphenicol, florfenicol, and thiamphenicol), ansamycins (for example, rifamide, rifampin, rifamycin sv, rifapentine, and rifaximin), β-lactams (for example, carbacephems, such as loracarbef; carbapenems, such as imipenem, meropenem, and panipenem; cephalosporins, such as cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, and pivcefalexin; cephamycins, such as cefbuperazone, cefmetazole, cefininox, cefotetan, and cefoxitin; and monobactams, such as aztreonam, carumonam, and tigemonam), oxacephems (for example, flomoxef and moxalactam), penicillins (for example, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin g benzathine, penicillin g benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin), other antibiotics (for example, ritipenem), lincosamides (for example, clindamycin and lincomycin), macrolides (for example, azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, and troleandomycin), polypeptides (for example, amphomycin, bacitracin, capreomycin, colistin, enduracidin, enviomycin, fusafungine, gramicidin(s), mikamycin, polymyxin, pristinamycin, ristocetin, teicoplanin, thiostrepton, tuberactinomycin, tyrocidine, tyrothricin, vancomycin, viomycin, virginiamycin, and zinc bacitracin), tetracyclines (for example, apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, and tetracycline), and others (e.g., cycloserine, mupirocin, and tuberin). Agents of use also include synthetic antibacterials, such as 2,4-Diaminopyrimidines (for example, brodimoprim, tetroxoprim, and trimethoprim), nitrofurans (for example, furaltadone, furazolium chloride, nifuradene, nifuratel, nifurfoline, nifurpirinol, nifurprazine, nifurtoinol, and nitrofurantoin), quinolones and analogs (for example, cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, and trovafloxacin), sulfonamides (for example, acetyl sulfamethoxypyrazine, benzylsulfamide, chloramine-b, chloramine-t, dichloramine-t, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, and sulfisoxazole), sulfones (for example, acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, and thiazolsulfone), and others (for example, clofoctol, hexedine, methenamine, methenamine anhydromethylene-citrate, methenamine hippurate, methenamine mandelate, methenamine sulfosalicylate, nitroxoline, taurolidine, and xibornol).

Further, additional therapeutic agents of use include antifungal antibiotics, such as polyenes (for example, amphotericin B, candicidin, dennostatin, filipin, fungichromin, hachimycin, hamycin, lucensomycin, mepartricin, natamycin, nystatin, pecilocin, and perimycin), others (for example, azaserine, griseofulvin, oligomycins, neomycin undecylenate, pyrrolnitrin, siccanin, tubercidin, and viridin), allylamines (for example, butenafine, naftifine, and terbinafine), imidazoles (for example, bifonazole, butoconazole, chlordantoin, chlormiidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, and tioconazole), thiocarbamates (for example, tolciclate, tolindate, and tolnaftate), triazoles (for example, fluconazole, itraconazole, saperconazole, and terconazole), and others (for example, acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, and zinc propionate).

Antineoplastic agents can also be additional therapeutic agents of use, including (1) antibiotics and analogs (for example, aclacinomycins, actinomycin, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, and zorubicin); (2) antimetabolites, such as folic acid analogs (for example, denopterin, edatrexate, methotrexate, piritrexim, pteropterin, TOMUDEX®, and trimetrexate); (3) purine analogs (for example, cladribine, fludarabine, 6-mercaptopurine, thiamiprine, and thioguanine); and (4) pyrimidine analogs (for example, ancitabine, azacitidine, 6-azauridine, carmofur, cytarabine, doxifluridine, emitefur, enocitabine, floxuridine, fluorouracil, gemcitabine, and tagafur).

Steroidal anti-inflammatory agents can also be included as additional therapeutic agents of use, such as 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, cyclosporine, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

In addition, non-steroidal anti-inflammatory agents can be used, including aminoarylcarboxylic acid derivatives (for example, enfenamic acid, etofenamate, flufenamic acid, isonixin, meclofenamic acid, mefenamic acid, niflumic acid, talniflumate, terofenamate, and tolfenamic acid), arylacetic acid derivatives (for example, aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, and zomepirac), arylbutyric acid derivatives (for example, bumadizon, butibufen, fenbufen, and xenbucin), arylcarboxylic acids (for example, clidanac, ketorolac, and tinoridine), arylpropionic acid derivatives (for example, alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, and zaltoprofen), pyrazoles (for example, difenamizole and epirizole), pyrazolones (for example, apazone, benzpiperylon, feprazone, mofebutazone, morazone, oxyphenbutazone, phenylbutazone, pipebuzone, propyphenazone, ramifenazone, suxibuzone and thiazolinobutazone), salicylic acid derivatives (for example, acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, and sulfasalazine), thiazinecarboxamides (for example, ampiroxicam, droxicam, isoxicam, lornoxicam, piroxicam, and tenoxicam), ε-acetamidocaproic acid, s-adenosylmethionine, 3-amino-4-hydroxybutyric acid, amixetrine, bendazac, benzydamine, α-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, zileuton, lifitegrast, and nepafenac. In addition to the above examples, other immunomodulatory agents that can be used include alkalating agents (e.g., cyclophosphamide and chlorambucil) and antimetabolites (e.g., azathioprine and mychephelonate mofetil).

Methods are provided herein for treating ocular surface inflammation or uveitis in a subject, such as a mammalian or a human subject. In some methods, the ocular surface inflammation or uveitis includes a Th17 response. The methods can include selecting a subject with uveitis and/or an ocular surface disease. The subject can have ocular surface inflammation, such as due to an ocular surface disease, for example, dry eye and non-dry eye conjunctivitis and keratitis, such as allergic conjunctivitis, infective and noninfective keratitis, and conjunctivitis, or due to inflammation from other external eye disease, such as non-dry eye lid disease, including meibomian gland dysfunction (MGD) and anterior blepharitis.

In some examples, the method includes selecting a subject with uveitis. Any form of uveitis can be treated using an IL-24 polypeptide, variant thereof, or fusion protein thereof or a nucleic acid molecule encoding the IL-24 polypeptide, variant thereof, or fusion protein thereof. The subject can have anterior uveitis (i.e., iridocyclitis or inflammation of the iris and the ciliary body and/or iritis), intermediate uveitis, posterior uveitis (i.e., chorioretinitis or inflammation of the choroid and retina), or diffuse uveitis (i.e., panuveitis). In some other examples, the uveitis can include iritis, cyclitis, cyclitis, pars planitis, chorioretinitis, iridocyclitis, or iritis. The methods can also be used to treat uveitis that is acute or chronic. In some examples, the uveitis can result from surgery, trauma, an autoimmune disorder, exposure to chemical stimuli, an infection, an inflammatory disorder, or the human leukocyte antigen B27 (HLA-B27) haplotype.

In one embodiment, a method is provided for treating anterior uveitis in a subject. Subjects can be treated that are affected with idiopathic iridocyclitis, HLA-B27-positive iridocyclitis, uveitis associated with juvenile rheumatoid arthritis, Fuch's heterochromatice iridocyclitis, herpes simplex keatovueitis, ankylosing spondylitis, intraocular lens related uveitis, Reiter's syndrome, Herpes zoster keratouveitis, uveitis associated with syphilis, traumatic iridocyclitis, uveitis associated with inflammatory bowel disease, and/or tuberculosis iridocyclitis.

In another embodiment, a method is provided for treating posterior uveitis in a subject. Thus, subjects can be treated that are affected with toxoplasma retinochroiditis, retinal vasculitis, idiopathic posterior uveitis, ocular histoplasmosis, toxocariasis, cytomegalovirus retinitis, idiopathic retinitis, serpinous choroidopathy, acute multifocal placoid, pigment eptiheliopathy, acute retinal necrosis, bird shot choroidopathy, uveitis associated with a leukemia or a lymphoma, reticulum cell sarcoma, ocular candidiasis, tuberculous uveitis, and/or lupus retinitis.

In a further embodiment, a method is provided for treating diffuse uveitis. Thus, subjects can be treated that are affected with sarcoidosis, syphilis, Vogt-Koyanagi-Harada syndrome, and/or Bechet's disease.

In one embodiment, a sign or a symptom of the uveitis is decreased or alleviated. Ocular signs include ciliary injection, aqueous flare, the accumulation of cells visible on ophthalmic examination (e.g., aqueous cells, retrolental cells, and vitreous cells), keratic precipitates, and hypema. Symptoms include pain (such as ciliary spasm), redness, photophobia, increased lacrimation, and decreased vision. One of skill in the art can readily diagnose uveitis. In one embodiment, biomicroscopy (for example, a "slit lamp") is used to diagnose uveitis, to evaluate the clinical course of the disease, or to verify that a treatment protocol has been successful.

The methods can be used to treat a subject with uveitis, where the subject has an autoimmune disorder. In some exemplary methods, the autoimmune disorder can be sarcoidosis, ankylosing spondylitis, arthritis, multiple sclerosis, or psoriasis. In other embodiments, the subject can have an inflammatory disorder. In some examples, the inflammatory disorder can be Crohn's disease, ulcerative colitis, or Behcet's syndrome. In additional exemplary methods, the subject can have an infection. In some methods, the infection can result from cat-scratch disease, herpes zoster, herpes simplex, leptospirosis, toxocariasis, toxoplasmosis, syphilis, tuberculosis, Lyme disease, West Nile virus, cytomegalovirus, or human immunodeficiency virus (HIV). In other embodiments, the subject can have the haplotype HLA-B27.

The methods can include selecting a subject with ocular surface disease. Any form of ocular surface inflammation, such as due to an ocular surface disease, can be treated using an IL-24 polypeptide, variant thereof, or fusion protein thereof or a nucleic acid molecule encoding the IL-24 polypeptide, variant thereof, or fusion protein thereof. In some embodiments, the ocular surface disease can be dry eye syndrome (DES), including DES associated with Sjögren syndrome (SS) and non-SS KCS, or conjunctivitis and keratitis, such as allergic conjunctivitis, infective and noninfective keratitis, and conjunctivitis.

In some embodiments, the methods can be used to treat ocular surface inflammation where a subject is selected that has keratitis. In certain examples, the methods can be used to treat bacterial keratitis or viral keratitis. In one specific non-liming example, methods are provided for treating keratitis caused by various microbial infections such as gram-negative bacteria (*P. aeruginosa* and *S. marcesans*), gram positive bacteria (for example, *S. aureus, S. epidermidis*, and *Corynebacterium* species (e.g., *P. acnes*)). In some embodiments, the keratitis is caused by gram positive cocci, gram negative bacilli, gram negative coccobacilli, gram positive bacilli, spirochetes, mycobacteria, or actinomycetes. In other embodiments, methods are provided for treating keratitis caused by a virus, such as an adenovirus, a herpes virus, a poxvirus, or a rubeola virus. In other examples, the methods can be used to treat keratitis that results from laser eye therapy, trauma, exposure to ultraviolet light, exposure to chemical stimuli, contact lens wear, conical transplant, exposure to a toxin, or autoimmune disease. In examples, where the keratitis results from autoimmune disease, the subject can have Sjögren's syndrome or rheumatoid arthritis. In still further examples, the methods can treat keratitis is ulcerative. In additional embodiments, keratitis can be treated in a subject, wherein the inflammation is associated with contact lens wear. These syndromes can include, but are not limited to contact lens associated corneal infiltrates (CLACI), contact lens associated red eye (CLARE), contact lens peripheral ulcer (CPLU). Sterile and infectious infiltrates can usually, but not always, be distinguished by slit lamp examination by those having ordinary skill in the art.

The methods can then include administering to the subject a therapeutically effective amount of an interleukin 24 (IL-24) polypeptide, a variant thereof (e.g., a conservative variant), or an Fc fusion protein thereof, wherein the polypeptide, variant (e.g., a conservative variant), or Fc fusion protein suppresses production of effector cytokines by Th17 cells, thereby treating the ocular surface inflammation in the subject. In some examples, the effector cytokines are IL-17A, IL-17F, IL-21, and/or IL-22. In some examples, the methods can include administering to the subject a therapeutically effective amount of a nucleic acid encoding the IL-24 polypeptide, variant thereof, or Fc fusion protein thereof, thereby treating the ocular surface inflammation in the subject.

Methods are also provided for treating conjunctivitis. The conjunctivitis can be conjunctivitis from an infectious agent, such as a virus. Viral conjunctivitis can be caused by an adenovirus, a herpes simplex virus, an enterovirus, or a coxsackievirus, among others. Bacterial conjunctivitis can be caused by *S. aureus, S. pneumoniae*, or *H. influenzae*, among others. The conjunctivitis can be caused by *N. gonorrhoeae* or *N. meningitidis*.

In specific non-limiting examples, the conjunctivitis is chronic bacterial conjunctivitis, such as conjunctivitis caused by *S. aureus, M. lacunata*, or other gram-negative enteric bacteria. The conjunctivitis can be associated with blepharitis.

The conjunctivitis can be chemically induced, such as from the introduction of an irritant, for example from the introduction of an acid or alkali substance into the eye. The conjunctivitis can be allergic conjunctivitis. Methods are also provided for treating blepharoconjunctivitis and keratoconjunctivitis. In specific, non-limiting examples, the keratoconjunctivitis is keratoconjunctivitis sicca, vernal keratoconjunctivitis, atopic keratoconjunctivitis, infectious bovine keratoconjunctivitis, superior limbic keratoconjunctivitis, or keratoconjunctivitis photoelectric a.

The methods can be used to treat ocular surface inflammation due to blepharitis. In specific, non-limiting examples, the blepharitis is seborrhoeic, staphylococcal, mixed, posterior (or meibomitis), or parasitic. The blepharitis can be posterior blepharitis or anterior blepharitis.

In additional embodiments, the subject can be administered an additional pharmaceutical agent, such as an anti-inflammatory agent, immunosuppressive agent, antibacterial agent, antifungal agent, or an immunomodulatory agent. The phrase "combinatorial therapy" or "combination therapy" embraces the administration of an IL-24 polypeptide, variant thereof, or fusion protein thereof or a nucleic acid molecule encoding the IL-24 polypeptide, variant thereof, or fusion protein thereof and one or more therapeutic agents as part of a specific treatment regimen intended to provide beneficial effect from the co-action of these therapeutic agents. Administration of these therapeutic agents in combination typically is carried out over a defined period (usually minutes, hours, days, or weeks, depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents or at least two of the therapeutic agents in a substantially simultaneous manner Substantially simultaneous administration can be accomplished, for example, by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, topical administration, oral routes, intravenous routes, intramuscular routes, and direct absorption through mucous membrane tissue. The therapeutic agents can be administered by the same route or by different routes. Any of the compositions disclosed above can be used in the presently claimed methods.

For any of the methods disclosed herein, the IL-24 polypeptide, variant thereof, or fusion protein thereof or nucleic acid molecule encoding the IL-24 polypeptide, variant thereof, or fusion protein thereof can be administered systemically or locally. In some embodiments, the IL-24 polypeptide, variant thereof, or fusion protein thereof or nucleic acid molecule encoding the IL-24 polypeptide, variant thereof, or fusion protein thereof is administered locally to the eye. The administration can be topical, such as in an ophthalmic solution or ointment, or in a contact lens placed in the eye. The IL-24 polypeptide, variant thereof, or fusion protein thereof or nucleic acid molecule encoding the IL-24 polypeptide, variant thereof, or fusion protein thereof can be included in an implant that is implanted in the eye. However, administration can also be systemic.

Any of the administration methods and/or compositions disclosed above can be utilized. More than one method of administration also can be utilized, such as a combination of instillation methods. For example, implants can be sequentially implanted into the vitreous in order to maintain concentrations for even long periods. In one embodiment, more than one implant can be sequentially implanted into the eye in order to maintain therapeutic drug concentrations for longer periods. Implants or contact lens can be combined with ophthalmic solutions or ointments. Topical administration can also be combined with systemic administration.

In one embodiment, a sign or a symptom of the inflammation is decreased or alleviated. Administration can be systemic or local. One polypeptide or polynucleotide, or multiple polypeptides and polynucleotides can be utilized.

EXAMPLES

Example 1

Methods and Materials

Induction of EAU and Disease Scoring

Experimental autoimmune uveitis (EAU) was induced by adoptive transfer. Lymph nodes from naïve WT or IL-17A KO R161H mice (B10.RIII background) were dispersed into single-cell suspensions and cultured in 12-well plates at $2 \times 10^6$ cells/ml ($5 \times 10^6$ cells/well). Cells were activated with 2 µg/ml of $IRBP_{161-180}$ under Th17 polarizing conditions in the presence of 25 ng/ml IL-6, 1 ng/ml of TGF-β, 10 µg/ml of anti-IFN-γ, and 10 µg/ml of anti-IL-4 for Th17 polarization. After 24 hrs, 10 ng/ml of IL-2 or IL-23 was added to the Th1 and Th17 cultures respectively. After 72 hrs, cells were purified by centrifugation over Lympholyte M (Cedarlane, Burlington, N.C.) and washed with 1×PBS. Approximately $4 \times 10^6$ cells were injected intraperitoneally into naïve B10.RIII mice. In some experiments, the recipient mice received recombinant IL-24 (100 µg per mouse, intraperitoneal injection) every other day.

Active EAU was induced by immunizing mice with the uveitogenic epitope of IRBP protein IRBP651-670 at 300 µg/mouse, emulsified 1:1 v/v in complete Freund's adjuvant containing 2.5 mg/ml *Mycobacterium tuberculosis* in a total volume of 200 µl and administered subcutaneously (100 µl at the base of the tail, 50 µl on each hind limb). Animals also received pertussis toxin from *Bordetella pertussis* at 1 µg/mouse in 100 µl medium containing 0.1% normal mouse serum and administered intraperitoneally.

Experimental autoimmune uveitis was evaluated by fundus examination on a scale of 0-4 based on the extent of inflammation (PMID: 15286397). Eyes were harvested at the end of experiments, processed for histopathology, and stained with standard hematoxylin and eosin. The severity of EAU was evaluated in a double blind study on a scale of 0-4 based on the number, type, and size of lesions (PMID: 15286397).

Induction of Experimental Autoimmune Encephalomyelitis (EAE) and Disease Scoring EAE was actively induced by immunizing mice with an encephalitogenic epitope of myelin oligodendrocyte glycoprotein protein (MOG), MOG35-55 (see, e.g., Sun et al., International Immunology, 15(2): 261-268, 2003), at 200 µg/mouse, emulsified 1:1 v/v in complete Freund's adjuvant containing 4.0 mg/ml *Mycobacterium tuberculosis* in a total volume of 200 and administered subcutaneously (100 µl at the base of the tail, 50 µl on each hind limb). Animals also received pertussis toxin from *Bordetella pertussis* at 0.3 µg/mouse in 100 µl medium containing 0.1% normal mouse serum and administered intraperitoneally on day 0 and day 2. Daily monitoring of animals and pain assessment were performed per the IACUC guidelines. The severity of disease was scored on a scale of 0-5 as previously described (Miller, S D and Karpus, W J, Current protocols in Immunology Unit 15.1, 2007), 0 being clinically normal, scores 1-4 being varying degrees of ascending paralysis from tail to fore limbs, and 5 being death.

Intra-Ocular Administration of Therapeutic Agents

For gene therapy using the adeno associated viral (AAV) delivery method, mice were anesthetized with a combination of ketamine and xylazine (77 mg/kg and 4.6 mg/kg, respectively), and $1.4 \times 10^9$ viral particles of either empty AAV8 (into the left eye) or AAV8-IL-24-eGFP (into the right eye) was injected sub-retinally as described previously (PMID 26274541).

T Cell Differentiation

Mouse $CD4^+CD62L^+$ T cells were purified from spleen using the $CD4^+CD62L^+$ T Cell Isolation Kit II (Miltenyi Biotech, Cambridge, Mass.). The cells were stimulated by plate-bound anti-CD3 (2 µg/ml) and soluble anti-CD28 (1 µg/ml). For Th1 polarization, cultures were supplemented with 10 ng/ml IL-6, 1 ng/ml TGF-β, 10 µg/ml anti-IFN-γ, and 10 µg/ml anti-IL-4. Where specified, 50 ng/ml of IL-17A was added to the cultures. On day 3, the cells were pulsed with PMA (50 ng/ml) and ionomycin (500 ng/ml) in the presence of brefeldin A (GolgiPlug; BD Pharmingen, San Diego, Calif.) for 4 hrs. The cells were then fixed with 4% paraformaldehyde and permeabilized with PBS containing 0.1% BSA and 0.05% Triton X-100 for intracellular cytokine staining using anti-IFN-γ, IL-17A, IL-17F, IL-22, and GM-CSF.

RNA-Seq

RNA samples were purified and fragmented. The library was then constructed as described previously (PMID: 22688717). Sequencing was performed using an Illumina GAIIx with SCS v2.10 software. Quality control (QC) was confirmed with FastQC v0.10.1 and was within expected levels for RNA-sq libraries (<1% of reads).

To visualize aligned reads, the reads were aligned using Bowtie2 v2.1.0 (PMID: 19261174, bowtie-bio.sourceforge.net, last accessed Apr. 19, 2017) for initial alignment to the transcriptome and then for alignment with the genome. TopHat2 v2.0.9 (PMID:19289445, ccb.jhu.edu, last accessed Apr. 19, 2017) was used to align to the mouse genome assembly GRCm38.p2. For annotation of the mouse RNA, Ensemble v73 was used. Samtools v0.1.19 was used to create BAM files for visualization in Integrative Genomics Viewer (PMID: 21221095).

To quantitate the aligned reads to the transcriptome, Bowtie2 v2.1.0 was used to align the reads to all possible transcripts, and eXpress v1.3.1 was used to assign the reads to transcript isoforms and for quantitation.

Principal component analysis (for replicate reproducibility), expression plots, and clustering were performed using the statistical environment 'R' (version 3.3.1), and a differential expression (DE) analysis was performed using EdgeR (PMID:19910308). The generalized linear model was used for multiple factor testing and batch correction before the DE analysis.

IL-24 Knockdown by siRNA

Cells were polarized under Th17 conditions with the specific antigen IRBP161-180 in the presence of Accell siRNA oligonucleotides that target IL-24 (Dharmacon, Lafayette, Colo.) and with 3% FCS as described previously (PMID: 20676095). The cells were harvested for adoptive transfer or cDNA synthesis.

Example 2

Results

The susceptibility to uveitis of spontaneously uveitic R161H mice (IRBP T cell receptor transgenic mice, PMID: 23810578) crossed onto the IL-17A−/− background was investigated. An IL-17A deficiency did not reduce the severity of uveitis in R161H mice (FIG. 1; IL-17A-sufficient in circles and IL-17A-deficient in squares). Furthermore, IL-17A-deficient (IL-17A−/− background) and IL-17A-sufficient R161H interstitial retinol-binding protein (IRBP)-specific T cells (lymph node, LN, cells) that were polarized under Th17 conditions and adoptively transferred into wild-type recipients induced similar disease levels compared to IL-17A-sufficient R161H T cells (FIG. 2; IL-17A-sufficient in squares and IL-17A-deficient in circles).

Figure 3B:
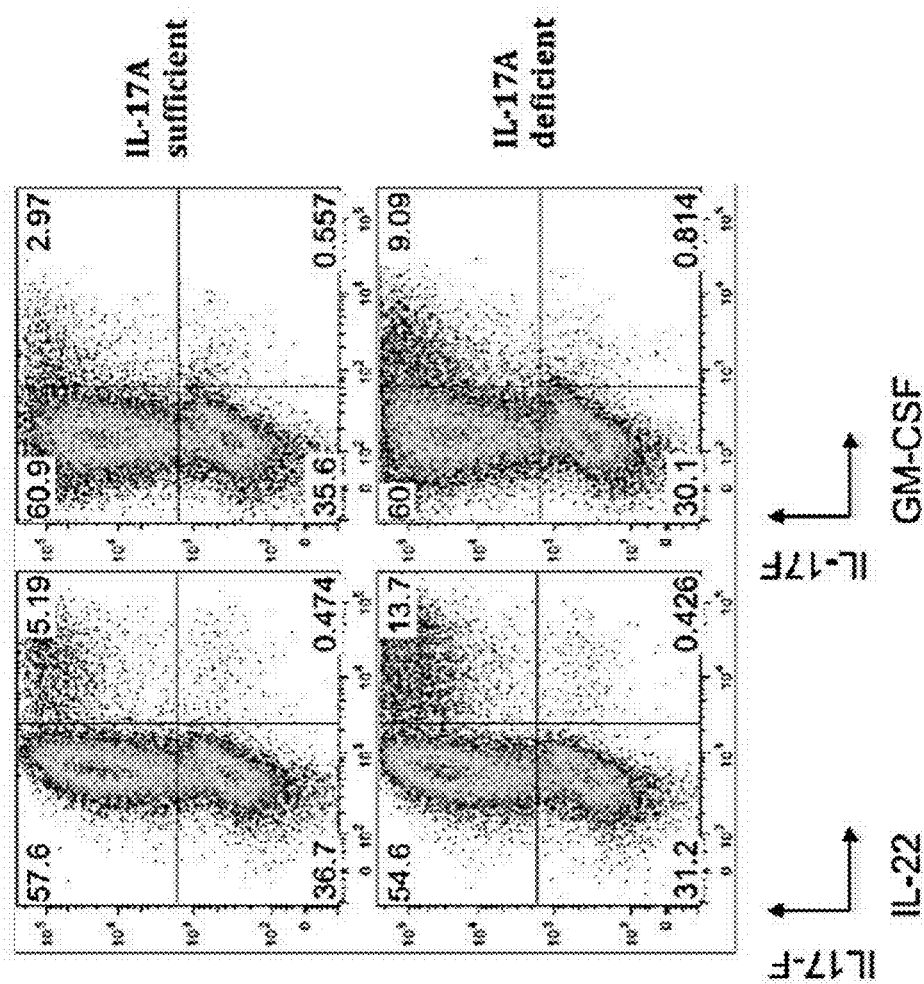
FIGS. 3A-3B show that IL-17A-deficient Th17 cells (bottom) produce higher levels of Th17-related cytokines (IL-17F and IL-22 (left) as well as granulocyte macrophage colony-stimulating factor (GM-CSF; right)) in vitro compared with IL-17A-sufficient Th17 cells (top).
Figure 3A:
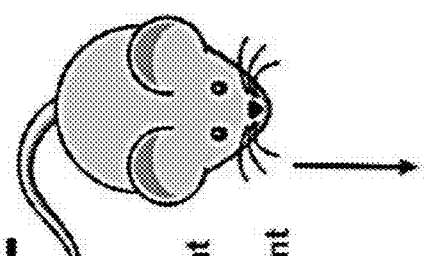
Figure 5A:
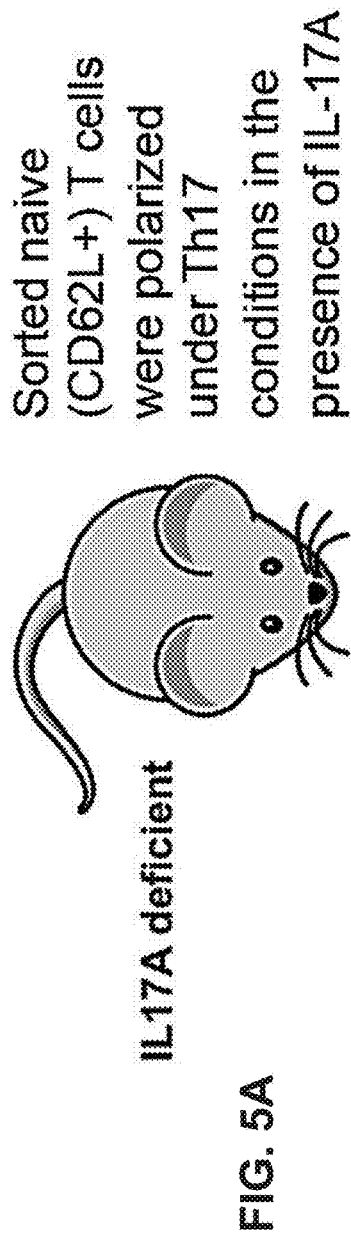
FIGS. 5A-5B show that IL-17A-deficient Th17 cells (middle) produce higher levels of Th17-related cytokines (IL-17F and GM-CSF) in vitro compared with IL-17A-sufficient Th17 cells (left). Recombinant (r) IL-17A was then added (right), mitigating the effect.
Figure 5B:
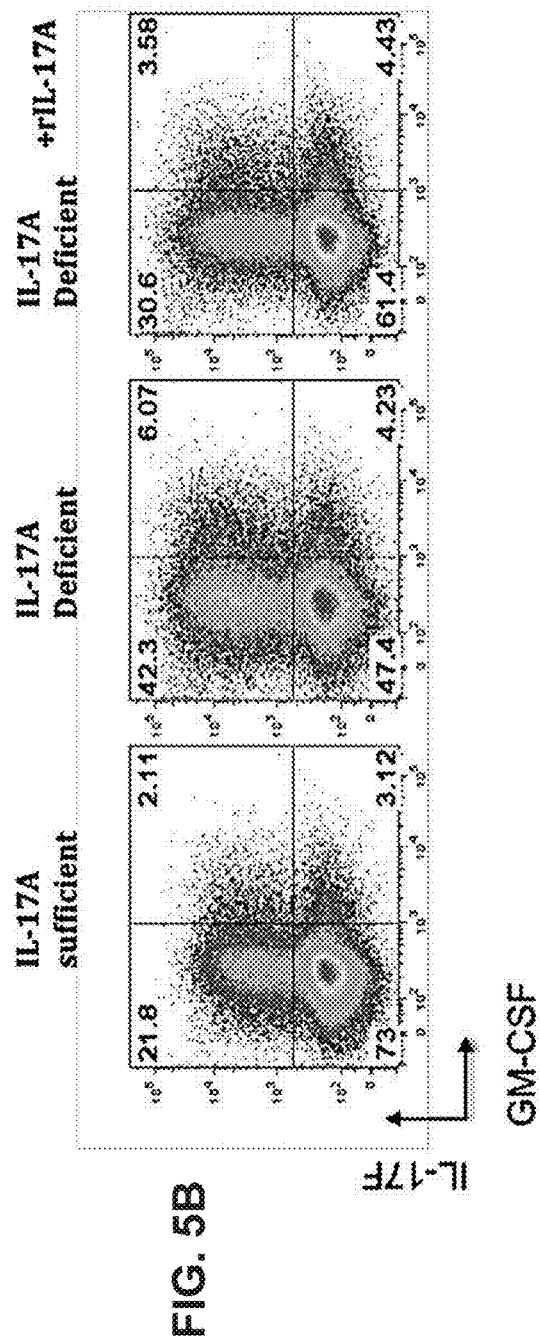

Further, the IL-17A−/−R161H 'Th17' cells produced elevated amounts of other Th17 lineage cytokines (IL-17F, GM-CSF, and IL-22; FIGS. 3-4). However, the elevated levels of other cytokines (IL-17F and GM-CSF) was reversed in sorted naïve (CD62L+) T cells polarized under Th17 conditions by supplementing the cultures with recombinant (r) IL-17A.

An RNAseq analysis of sorted naïve (CD62L+) T cells polarized under Th17 conditions revealed that IL-17A−/− Th17 cells had reduced IL-24 expression compared with their IL-17-sufficient counterparts (FIG. 6). Further, in sorted naïve (CD62L+CD4+) T cells polarized under Th17 conditions, rIL-24 suppresses production of effector cytokines by Th17 cells (FIG. 7).

Figure 8B:
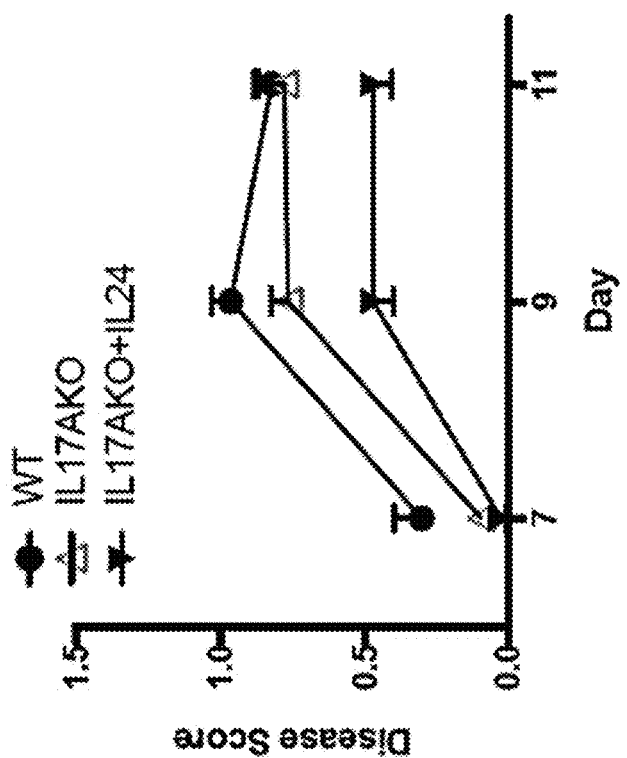
FIGS. 8A-8B show the effect of adding small interfering (si) IL-24 RNA to wild-type (wt) cells (left), which show increases uveitis severity, compared with adding IL-24 to IL-17 knock-out (IL-17KO) cells, which inhibits the ability of Th17 cells to induce EAU.
Figure 8A:
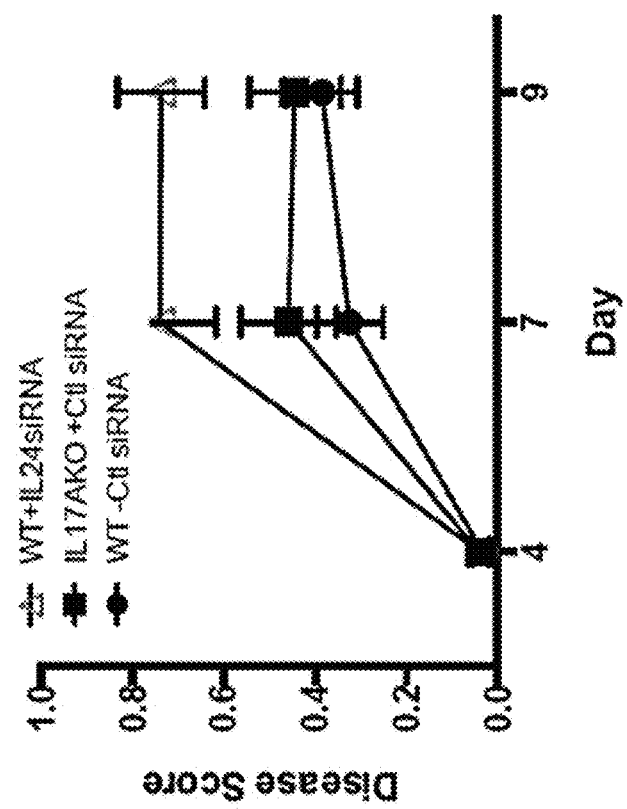
Figure 9A:
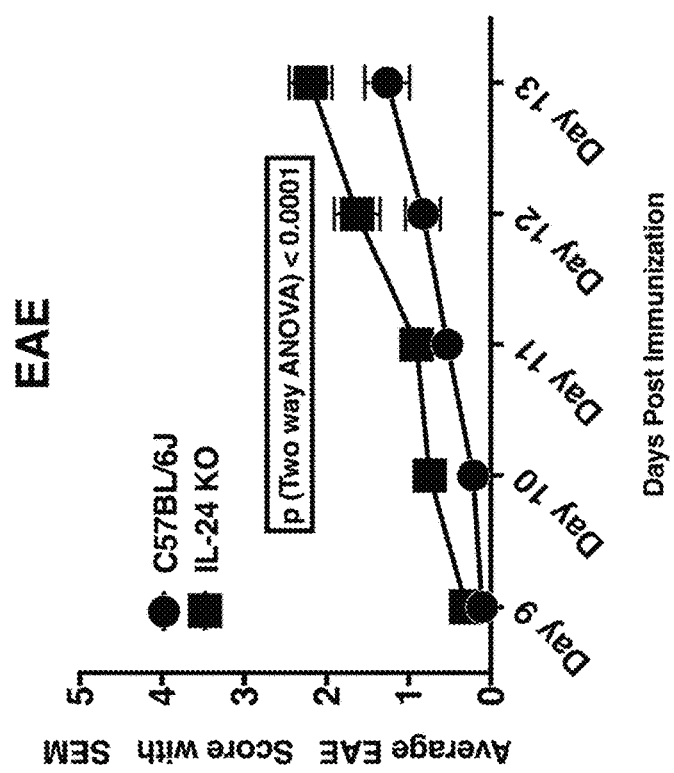
FIGS. 9A-9B are a pair of graphs showing congenital deficiency of IL-24 augment severity of experimental autoimmune diseases of the central nervous system in animal models. EAU and EAE diseases were induced in C57BL/6J and IL-24 KO strains of mice using the respective autoantigens, and the severity of the diseases were scored as described in the Example 1. Experiments for each disease model were repeated twice. The combined data from two experiments are shown. The data were analyzed using a two-way ANOVA test.
Figure 9B:
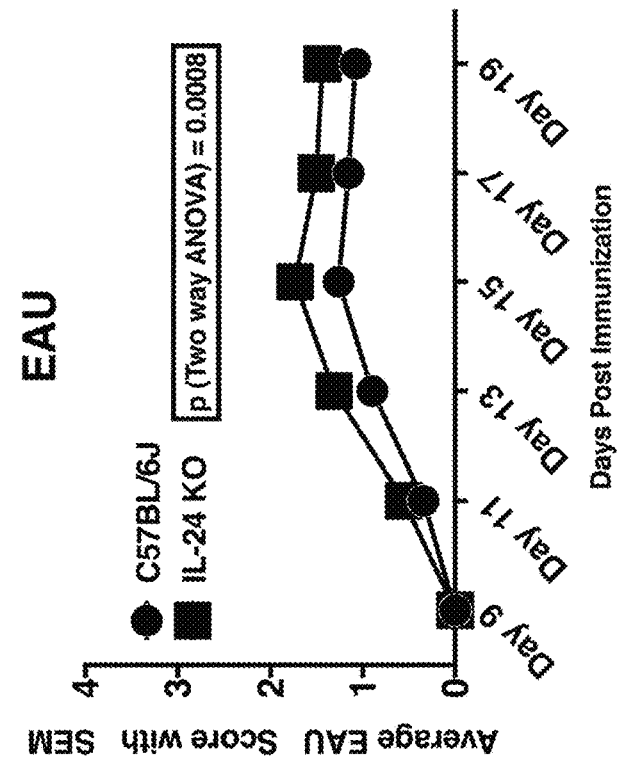
Figure 10:
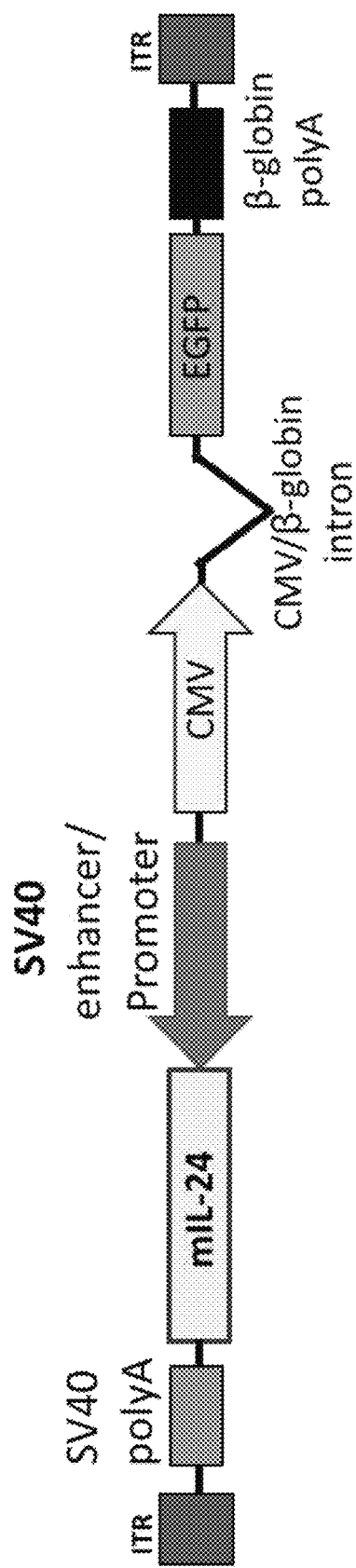
FIG. 10 is a schematic representation of AAV8-eGFP-mIL-24 construct for gene therapy. An AAV8-eGFP-mIL-24 construct was generated using the full-length cDNA sequence of murine IL-24 (GENBANK® Accession No. NM_053095.2, incorporated herein by reference). The vector plasmid contains two ITRs from AAV2 separated by a CMV promoter, a chimeric intron derived from CMV and beta globin, an eGFP coding sequence, and a polyadenylation signal from beta globin for the expression of green fluorescent protein (GFP) in one direction and an SV40 enhancer and promoter, a murine IL-24 coding sequence, and a polyadenylation signal from SV40 to drive the expression of murine IL-24. Outside of the two ITRs is the bacterial backbone containing an amp R gene.
Figure 11:
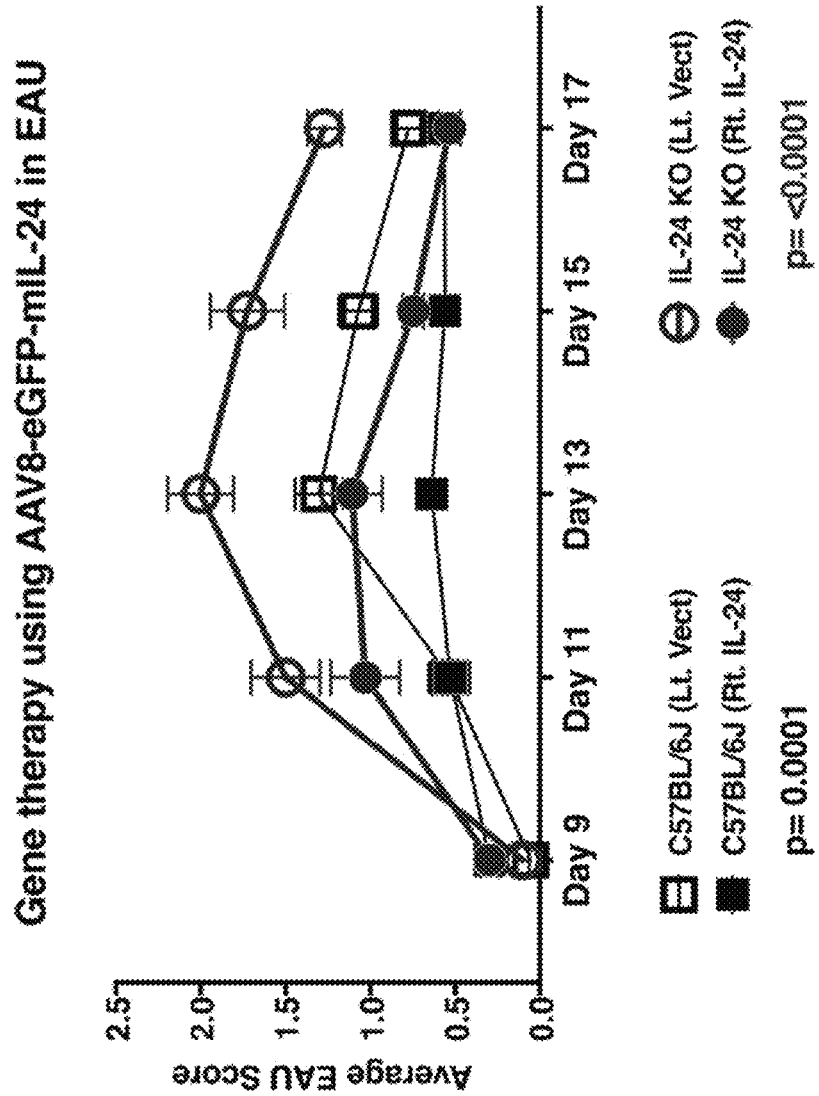
FIG. 11 shows that exogenous expression of murine IL-24 in the ocular tissue ameliorates disease severity and progression of EAU in wild type as well as in IL-24-deficient mice. Mice were intra-ocularly (sub-retinal) injected with an empty null vector AAV8 in the left eye or an AAV8-eGFP-mIL-24 expression cassette in the right eye 10-12 days prior to induction of EAU to allow adequate time for expression of the murine IL-24 protein in the right eyes. Mice were challenged for EAU disease by immunization with an IRBP peptide. Combined data from two separate experiments are shown. Disease severity in both eyes was scored and analyzed using a two-way ANOVA.

Moreover, when short interfering (si) RNA for IL-24 was added to wild-type (wt) cells, the cells show greater levels of EAU, which is in contrast to wild-type (wt) only and IL-17 knock out (KO) mice (FIG. 8, left). However, adding IL-24 to wt mice showed lower levels of EAU, which is in contrast to wt only and IL-17KO mice (FIG. 8, right). Thus, IL-24 inhibits the ability of Th17 cells ability to induce EAU.

These data show that (a) IL-17A is not necessary for the pathogenicity of uveitogenic Th17 cells and (b) IL-17A exerts feedback inhibition on Th17 cells to control expression of other Th17-related cytokines. Thus, an IL-17A deficiency does not reduce spontaneous uveitis in R161H mice and does not reduce the pathogenicity of autoreactive Th17 cells. However, an IL-17A deficiency does enhance production of other lineage-associated pathogenic cytokines (e.g., IL-17F, IL-22, and GM-CSF) in Th17 cells, which can be reversed by rIL-17A. Finally, a gene expression profile of IL-17A-deficient and IL-17A-sufficient Th17 cells reveals lower IL-24 expression in Th17 cells in association with IL-17A deficiency. Studies in vivo showed that injection of rIL-24 ameliorated adoptive Th17-induced EAU, and, conversely, silencing IL-24 expression in the adoptively transferred Th17 cells increased their pathogenicity and enhanced disease severity (FIG. 8). Thus, administration of IL-24 can be used for treating ocular inflammatory disorders, such as uveitis.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

---

We claim:

1. A method for treating ocular surface inflammation and/or uveitis in a subject, comprising:
selecting a subject with uveitis and/or an ocular surface disease; and
administering to the subject a therapeutically effective amount of:
(a) an interleukin 24 (IL-24) polypeptide or an Fc fusion protein thereof, wherein the polypeptide or Fc fusion protein suppresses production of effector cytokines by Th17 cells, or
(b) a nucleic acid molecule encoding the IL-24 polypeptide or Fc fusion protein thereof, thereby treating the ocular surface inflammation and/or uveitis in the subject.

2. The method of claim 1, comprising administering to the subject a therapeutically effective amount of:
(a) the polypeptide, wherein the polypeptide comprises the amino acid sequence of SEQ ID NO: 1 or SEQ ID NO: 2; or
(b) the nucleic acid molecule, wherein the nucleic acid molecule encodes the polypeptide of SEQ ID NO: 1 or SEQ ID NO: 2.

3. The method of claim 1, comprising administering to the subject a viral vector comprising a promoter operably linked to the nucleic acid molecule.

4. The method of claim 3, wherein the viral vector is an adeno-associated viral (AAV) vector.

5. The method of claim 4, wherein the AAV vector is an AAV8 vector.

6. The method of claim 1, wherein the ocular inflammation comprises a Th17 response.

7. The method of claim 1, comprising selecting the subject with uveitis, wherein the uveitis comprises anterior uveitis, intermediate uveitis, posterior uveitis, diffuse uveitis, iritis, cyclitis, cyclitis, pars planitis, chorioretinitis, iridocyclitis, and/or iritis.

8. The method of claim 1, comprising selecting the subject with uveitis, wherein the uveitis results from surgery, trauma, an autoimmune disorder, exposure to chemical stimuli, an infection, an inflammatory disorder, and/or the human leukocyte antigen B27 (HLA-B27) haplotype.

9. The method of claim 1, comprising selecting the subject with uveitis, wherein the subject has an autoimmune disorder, and wherein the autoimmune disorder is sarcoidosis, ankylosing spondylitis, arthritis, multiple sclerosis, and/or psoriasis.

10. The method of claim 1, comprising selecting the subject with uveitis, wherein the subject has an inflammatory disorder, and wherein the inflammatory disorder comprises Crohn's disease, ulcerative colitis, and/or Behcet's syndrome.

11. The method of claim 1, comprising selecting the subject with uveitis, and wherein the subject has an infection, and wherein the infection results from cat-scratch disease, herpes zoster, herpes simplex, leptospirosis, toxocariasis, toxoplasmosis, syphilis, tuberculosis, Lyme disease, West Nile virus, cytomegalovirus, and/or human immunodeficiency virus (HIV).

12. The method of claim 1, comprising selecting the subject with the ocular surface disease, and wherein the subject has dry eye, non-dry eye lid disease, non-dry eye conjunctivitis, and/or keratitis.

13. The method of claim 12, wherein the subject has keratitis, wherein (a) the keratitis is bacterial keratitis or viral keratitis; (b) wherein the keratitis results from laser eye therapy, trauma, exposure to ultraviolet light, exposure to chemical stimuli, contact lens wear, corneal transplant, exposure to a toxin, or autoimmune disease; and/or (c) is ulcerative.

14. The method of claim 12, wherein the subject has Sjögren's syndrome.

15. The method of claim 1, further comprising administering a therapeutically effective amount of at least one of an additional anti-inflammatory agent, immunosuppressive agent, antibacterial agent, antifungal agent, and/or an immunomodulatory agent to the subject.

16. The method of claim 15, wherein:
(i) the additional anti-inflammatory agent, immunosuppressive agent, and/or immunomodulatory agent is a glucocorticoid; or
(ii) the additional anti-inflammatory agent, immunosuppressive agent, antifungal agent, and/or immunomodulatory agent is a calcineurin antagonist.

17. The method of claim 1, wherein the subject is a human.

18. The method of claim 1, wherein the IL-24 polypeptide or the nucleic acid molecule is administered systemically to the subject.

19. The method of claim 1, further comprising administering the IL-24 polypeptide or the nucleic acid molecule in an excipient, wherein the polypeptide or the nucleic acid molecule is released as the excipient degrades.

20. The method of claim 19, wherein the excipient is a liposome.

21. The method of claim 1, further comprising administering an agent that increases the half-life of the IL-24 polypeptide or the nucleic acid molecule.

22. The method of claim 21, wherein the agent is an antibody that specifically binds the IL-24 polypeptide.

23. The method of any one of claims 12-14, wherein the IL-24 polypeptide or the nucleic acid molecule is administered topically to the eye of the subject.

24. The method of claim 23, wherein the polypeptide or the nucleic acid molecule is formulated in an ointment or solution for administration to the eye.

* * * * *

SEQUENCE LISTING

```
<160> NUMBER OF SEQ ID NOS: 5

<210> SEQ ID NO 1
<211> LENGTH: 207
<212> TYPE: PRT
<213> ORGANISM: Homo sapiens

<400> SEQUENCE: 1

Met Asn Phe Gln Gln Arg Leu Gln Ser Leu Trp Thr Leu Ala Ser Arg
1               5                   10                  15

Pro Phe Cys Pro Pro Leu Leu Ala Thr Ala Ser Gln Met Gln Met Val
            20                  25                  30

Val Leu Pro Cys Leu Gly Phe Thr Leu Leu Leu Trp Ser Gln Val Ser
        35                  40                  45

Gly Ala Gln Gly Gln Glu Phe His Phe Gly Pro Cys Gln Val Lys Gly
    50                  55                  60

Val Val Pro Gln Lys Leu Trp Glu Ala Phe Trp Ala Val Lys Asp Thr
65                  70                  75                  80

Met Gln Ala Gln Asp Asn Ile Thr Ser Ala Arg Leu Leu Gln Gln Glu
                85                  90                  95

Val Leu Gln Asn Val Ser Asp Ala Glu Ser Cys Tyr Leu Val His Thr
            100                 105                 110

Leu Leu Glu Phe Tyr Leu Lys Thr Val Phe Lys Asn Tyr His Asn Arg
        115                 120                 125
```

```
Thr Val Glu Val Arg Thr Leu Lys Ser Phe Ser Thr Leu Ala Asn Asn
    130                 135                 140

Phe Val Leu Ile Val Ser Gln Leu Gln Pro Ser Gln Glu Asn Glu Met
145                 150                 155                 160

Phe Ser Ile Arg Asp Ser Ala His Arg Arg Phe Leu Leu Phe Arg Arg
                165                 170                 175

Ala Phe Lys Gln Leu Asp Val Glu Ala Ala Leu Thr Lys Ala Leu Gly
                180                 185                 190

Glu Val Asp Ile Leu Leu Thr Trp Met Gln Lys Phe Tyr Lys Leu
                195                 200                 205
```

<210> SEQ ID NO 2
<211> LENGTH: 220
<212> TYPE: PRT
<213> ORGANISM: Mus musculus

<400> SEQUENCE: 2

```
Met Leu Thr Glu Pro Ala Gln Leu Phe Val His Lys Lys Asn Gln Pro
1               5                   10                  15

Pro Ser His Ser Ser Leu Arg Leu His Phe Arg Thr Leu Ala Gly Ala
                20                  25                  30

Leu Ala Leu Ser Ser Thr Gln Met Ser Trp Gly Leu Gln Ile Leu Pro
            35                  40                  45

Cys Leu Ser Leu Ile Leu Leu Trp Asn Gln Val Pro Gly Leu Glu
    50                  55                  60

Gly Gln Glu Phe Arg Phe Gly Ser Cys Gln Val Thr Gly Val Val Leu
65                  70                  75                  80

Pro Glu Leu Trp Glu Ala Phe Trp Thr Val Lys Asn Thr Val Gln Thr
                85                  90                  95

Gln Asp Asp Ile Thr Ser Ile Arg Leu Leu Lys Pro Gln Val Leu Arg
                100                 105                 110

Asn Val Ser Gly Ala Glu Ser Cys Tyr Leu Ala His Ser Leu Leu Lys
                115                 120                 125

Phe Tyr Leu Asn Thr Val Phe Lys Asn Tyr His Ser Lys Ile Ala Lys
    130                 135                 140

Phe Lys Val Leu Arg Ser Phe Ser Thr Leu Ala Asn Asn Phe Ile Val
145                 150                 155                 160

Ile Met Ser Gln Leu Gln Pro Ser Lys Asp Asn Ser Met Leu Pro Ile
                165                 170                 175

Ser Glu Ser Ala His Gln Arg Phe Leu Leu Phe Arg Arg Ala Phe Lys
                180                 185                 190

Gln Leu Asp Thr Glu Val Ala Leu Val Lys Ala Phe Gly Glu Val Asp
                195                 200                 205

Ile Leu Leu Thr Trp Met Gln Lys Phe Tyr His Leu
    210                 215                 220
```

<210> SEQ ID NO 3
<211> LENGTH: 618
<212> TYPE: DNA
<213> ORGANISM: Homo sapiens

<400> SEQUENCE: 3

```
atgaattttc aacagaggct gcaaagcctg tggactttag ccagaccctt ctgccctcct    60
ttgctggcga cagcctctca atgcagatg gttgtgctcc cttgcctggg ttttaccctg   120
cttctctgga gccaggtatc aggggcccag ggccaagaat ccactttgg gccctgccaa   180
```

```
gtgaaggggg ttgttcccca gaaactgtgg gaagccttct gggctgtgaa agacactatg    240
caagctcagg ataacatcac gagtgcccgg ctgctgcagc aggaggttct gcagaacgtc    300
tcggatgctg agagctgtta ccttgtccac accctgctgg agttctactt gaaaactgtt    360
ttcaaaaact accacaatag aacagttgaa gtcaggactc tgaagtcatt ctctactctg    420
gccaacaact tgttctcat cgtgtcacaa ctgcaaccca gtcaagaaaa tgagatgttt     480
tccatcagag acagtgcaca caggcggttt ctgctattcc ggagagcatt caaacagttg    540
gacgtagaag cagctctgac caaagccctt ggggaagtgg acattcttct gacctggatg    600
cagaaattct acaagctc                                                   618

<210> SEQ ID NO 4
<211> LENGTH: 660
<212> TYPE: DNA
<213> ORGANISM: Mus musculus

<400> SEQUENCE: 4
atgctgactg agcctgccca acttttgtg cacaagaaga accagccacc ttcacacagc      60
agcctccggc ttcactttag gaccctagca ggagcactgg ccctttcttc aacacagatg    120
agttggggac tacagattct ccctgcctg agcctaatcc ttcttctttg gaaccaagtg     180
ccagggcttg agggtcaaga gttccgattt gggtcttgcc aagtgacagg ggtggttctc    240
ccagaactgt gggaggcctt ctggactgtg aagaacactg tgcaaactca ggatgacatc    300
acaagcatcc ggctgttgaa gccgcaggtt ctgcggaatg tctcgggtgc tgagagctgt    360
taccttgccc acagctgct gaagttctac ttgaacactg ttttcaagaa ctaccacagc     420
aaaatagcca aattcaaggt cttgaggtca ttctccactc tggccaacaa cttcatagtc    480
atcatgtcac aactacagcc cagtaaggac aattccatgc ttcccattag tgagagtgca    540
caccagcggt ttttgctgtt ccgcagagca ttcaaacagt tggatacaga agtcgctttg    600
gtgaaagcct tggggaagt ggacattctc ctgacctgga tgcagaaatt ctaccatctc     660

<210> SEQ ID NO 5
<211> LENGTH: 684
<212> TYPE: DNA
<213> ORGANISM: Mus musculus

<400> SEQUENCE: 5
gaagcttgcc accatgctga ctgagcctgc ccaactttt gtgcacaaga agaaccagcc      60
accttcacac agcagcctcc ggcttcactt taggaccta gcaggagcac tggccctttc     120
ttcaacacag atgagttggg gactacagat tctcccctgc ctgagcctaa tccttcttct    180
ttggaaccaa gtgccagggc ttgagggtca agagttccga tttgggtctt gccaagtgac    240
aggggtggtt ctcccagaac tgtgggaggc cttctggact gtgaagaaca ctgtgcaaac    300
tcaggatgac atcacaagca tccggctgtt gaagccgcag gttctgcgga atgtctcggg    360
tgctgagagc tgttaccttg cccacagcct gctgaagttc tacttgaaca ctgttttcaa    420
gaactaccac agcaaaatag ccaaattcaa ggtcttgagg tcattctcca ctctggccaa    480
caacttcata gtcatcatgt cacaactaca gcccagtaag gacaattcca tgcttcccat    540
tagtgagagt gcacaccagc ggttttgct gttccgcaga gcattcaaac agttggatac    600
agaagtcgct ttggtgaaag ccttgggga agtggacatt ctcctgacct ggatgcagaa    660
attctaccat ctctgattct agag                                            684
```